US009359271B2

(12) United States Patent
LeViness et al.

(10) Patent No.: US 9,359,271 B2
(45) Date of Patent: *Jun. 7, 2016

(54) FISCHER-TROPSCH PROCESS

(71) Applicant: Velocys, Inc., Plain City, OH (US)

(72) Inventors: Stephen Claude LeViness, Columbus, OH (US); Francis Daly, Waldoboro, ME (US); Laura Amanda Richard, Abingdon (GB); Sreekala Rugmini, Kerala (IN)

(73) Assignee: Velocys, Inc., Plain City, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/680,399

(22) Filed: Apr. 7, 2015

(65) Prior Publication Data
US 2015/0210606 A1    Jul. 30, 2015

Related U.S. Application Data

(63) Continuation of application No. 13/802,921, filed on Mar. 14, 2013, now Pat. No. 9,006,298.

(60) Provisional application No. 61/716,772, filed on Oct. 22, 2012.

(51) Int. Cl.
*C07C 1/04* (2006.01)
*B01J 23/89* (2006.01)
(Continued)

(52) U.S. Cl.
CPC . *C07C 1/043* (2013.01); *B01J 8/00* (2013.01); *B01J 19/0093* (2013.01); *B01J 21/08* (2013.01);
(Continued)

(58) Field of Classification Search
CPC ........ B01J 19/0093; B01J 21/06; B01J 21/08; B01J 2208/00796; B01J 2219/00781; B01J 23/26; B01J 23/34; B01J 23/75; B01J 23/8913; B01J 23/8986; B01J 23/8993; B01J 35/0046; B01J 35/0053; B01J 35/006; B01J 35/0066; B01J 35/1014; B01J 35/1019; B01J 35/1038; B01J 35/1042; B01J 35/1061; B01J 37/0203; B01J 37/0205; B01J 37/0207; B01J 37/0213; B01J 37/08; B01J 37/088; B01J 37/16; B01J 37/18; B01J 8/00; C07C 1/043; C10G 2/33; C10G 2/332; C10G 2/333; C10G 2/34; C10G 2/341
USPC ........................................................ 518/715
See application file for complete search history.

(56) References Cited

U.S. PATENT DOCUMENTS 3,882,049 A    5/1975  Bertolacini et al. .......... 252/466
3,972,837 A    8/1976  Acres et al.
(Continued)

FOREIGN PATENT DOCUMENTS

DE            246257        6/1987
DE       39 26 466 A1       2/1991
(Continued)

OTHER PUBLICATIONS

Deshmukh ("Scale-Up of Microchannel Reactors for Fischer-Tropsch Synthesis" Ind Eng. Chem. Res. 2010, 49, 10883-10888, published on Aug. 5, 2010).*
(Continued)

*Primary Examiner* — Jafar Parsa
*Assistant Examiner* — Amy C Bonaparte
(74) *Attorney, Agent, or Firm* — Renner, Otto, Boisselle & Sklar, LLP

(57) ABSTRACT

The disclosed invention relates to a process for conducting a Fischer-Tropsch reaction, comprising flowing a reactant mixture comprising fresh synthesis gas and tail gas in a microchannel reactor in contact with a catalyst to form at least one hydrocarbon product, the catalyst being derived from a catalyst precursor comprising cobalt and a surface modified catalyst support.

62 Claims, 7 Drawing Sheets

(51) Int. Cl.
*B01J 37/18* (2006.01)
*B01J 19/00* (2006.01)
*B01J 37/02* (2006.01)
*B01J 8/00* (2006.01)
*B01J 35/00* (2006.01)
*B01J 35/10* (2006.01)
*B01J 37/08* (2006.01)
*B01J 21/08* (2006.01)
*B01J 23/26* (2006.01)
*B01J 23/34* (2006.01)
*C10G 2/00* (2006.01)
*B01J 37/16* (2006.01)

(52) U.S. Cl.
CPC *B01J 23/26* (2013.01); *B01J 23/34* (2013.01); *B01J 23/8913* (2013.01); *B01J 23/8993* (2013.01); *B01J 35/006* (2013.01); *B01J 35/0046* (2013.01); *B01J 35/0053* (2013.01); *B01J 35/0066* (2013.01); *B01J 35/1014* (2013.01); *B01J 35/1019* (2013.01); *B01J 35/1038* (2013.01); *B01J 35/1042* (2013.01); *B01J 35/1061* (2013.01); *B01J 37/0203* (2013.01); *B01J 37/0205* (2013.01); *B01J 37/0207* (2013.01); *B01J 37/0213* (2013.01); *B01J 37/08* (2013.01); *B01J 37/088* (2013.01); *B01J 37/16* (2013.01); *B01J 37/18* (2013.01); *C10G 2/33* (2013.01); *C10G 2/333* (2013.01); *C10G 2/34* (2013.01); *B01J 23/8986* (2013.01); *B01J 2208/00796* (2013.01); *B01J 2219/00781* (2013.01); *B01J 2219/00835* (2013.01); *B01J 2219/00873* (2013.01)

(56) References Cited

U.S. PATENT DOCUMENTS

| | | | |
|---|---|---|---|
| 4,089,810 A | 5/1978 | Diwell et al. | |
| 4,096,095 A | 6/1978 | Cairns | |
| 4,289,652 A | 9/1981 | Hunter et al. | |
| 4,392,362 A | 7/1983 | Little | 62/514 |
| 4,516,632 A | 5/1985 | Swift et al. | 165/167 |
| 4,585,798 A | 4/1986 | Beuther et al. | 518/715 |
| 4,738,948 A | 4/1988 | Iglesia et al. | 502/325 |
| 5,036,032 A | 7/1991 | Iglesia et al. | 502/260 |
| 5,248,251 A | 9/1993 | Dalla Betta et al. | |
| 5,309,637 A | 5/1994 | Moriarty | 29/890.054 |
| 5,317,805 A | 6/1994 | Hoopman et al. | 29/890.03 |
| 5,382,741 A | 1/1995 | Astbury et al. | 585/652 |
| 5,534,328 A | 7/1996 | Ashmead et al. | 428/166 |
| 5,569,455 A | 10/1996 | Fukui et al. | 422/174 |
| 5,611,214 A | 3/1997 | Wegeng et al. | 62/498 |
| 5,727,618 A | 3/1998 | Mundinger et al. | 165/80.4 |
| 5,733,839 A | 3/1998 | Epinoza et al. | 502/336 |
| 5,811,062 A | 9/1998 | Wegeng et al. | 422/129 |
| 5,858,314 A | 1/1999 | Hsu et al. | 422/211 |
| 6,040,266 A | 3/2000 | Fay, III et al. | |
| 6,075,062 A | 6/2000 | Zennaro et al. | 518/715 |
| 6,090,742 A | 7/2000 | Culross | |
| 6,121,190 A | 9/2000 | Zennaro et al. | |
| 6,126,723 A | 10/2000 | Drost et al. | 96/4 |
| 6,129,973 A | 10/2000 | Martin et al. | 428/166 |
| 6,136,868 A | 10/2000 | Culross et al. | 518/700 |
| 6,156,698 A | 12/2000 | Lida et al. | 502/439 |
| 6,192,596 B1 | 2/2001 | Bennett et al. | 34/76 |
| 6,200,536 B1 | 3/2001 | Tonkovich et al. | 422/177 |
| 6,211,255 B1 | 4/2001 | Schanke et al. | 518/715 |
| 6,216,343 B1 | 4/2001 | Leland et al. | 29/890.032 |
| 6,220,497 B1 | 4/2001 | Benz et al. | 228/118 |
| 6,230,408 B1 | 5/2001 | Ehrfeld et al. | 29/890.039 |
| 6,262,131 B1 | 7/2001 | Arcuri et al. | 518/700 |
| 6,313,393 B1 | 11/2001 | Drost | 136/201 |
| 6,352,577 B1 | 3/2002 | Martin et al. | 96/4 |
| 6,353,035 B2 | 3/2002 | Manzer et al. | 518/700 |
| 6,368,997 B2 | 4/2002 | Herron et al. | 502/302 |
| 6,381,846 B2 | 5/2002 | Insley et al. | 29/890.039 |
| 6,415,860 B1 | 7/2002 | Kelly et al. | 165/748 |
| 6,440,895 B1 | 8/2002 | Tonkovich et al. | |
| 6,451,864 B1 | 9/2002 | Wang et al. | 518/715 |
| 6,476,085 B2 | 11/2002 | Manzer et al. | 518/715 |
| 6,479,428 B1 | 11/2002 | Tonkovich et al. | 502/302 |
| 6,488,838 B1 | 12/2002 | Tonkovich et al. | 208/108 |
| 6,491,880 B1 | 12/2002 | Wang et al. | 422/211 |
| 6,537,945 B2 | 3/2003 | Singleton et al. | 502/327 |
| 6,540,975 B2 | 4/2003 | Tonkovich et al. | 423/659 |
| 6,558,634 B1 | 5/2003 | Wang et al. | 422/173 |
| 6,660,237 B2 | 12/2003 | Wang et al. | 422/222 |
| 6,675,875 B1 | 1/2004 | Vafai et al. | 165/80.4 |
| 6,746,651 B1 | 6/2004 | Ponzo et al. | 422/220 |
| 6,746,819 B1 | 6/2004 | Schmitz et al. | 430/272.1 |
| 6,747,178 B1 | 6/2004 | Harston et al. | 570/175 |
| 6,749,814 B1 | 6/2004 | Bergh et al. | 422/130 |
| 6,749,817 B1 | 6/2004 | Mulvaney, III | 422/200 |
| 6,755,211 B1 | 6/2004 | O'Connor et al. | 137/554 |
| 6,756,340 B2 | 6/2004 | Voskoboynikov et al. | 502/328 |
| 6,756,515 B2 | 6/2004 | Rende et al. | 585/444 |
| 6,764,660 B1 | 7/2004 | Wiede, Jr. et al. | 422/198 |
| 6,769,444 B2 | 8/2004 | Guzman et al. | 137/15.01 |
| 6,770,245 B2 | 8/2004 | Akporiaye et al. | 422/82.12 |
| 6,773,684 B2 | 8/2004 | Lesieur et al. | 422/198 |
| 6,824,689 B2 | 11/2004 | Wang et al. | |
| 7,045,486 B2 | 5/2006 | Wang et al. | 502/439 |
| 7,084,180 B2* | 8/2006 | Wang | B01J 19/0093 518/700 |
| 7,722,833 B2 | 5/2010 | Wang et al. | 422/198 |
| 7,829,602 B2 | 11/2010 | Litt et al. | |
| 8,100,996 B2 | 1/2012 | Simmons et al. | 48/197 |
| 9,006,298 B2* | 4/2015 | LeViness | B01J 23/8913 518/715 |
| 9,023,900 B2* | 5/2015 | Wang | B01J 23/75 502/325 |
| 2002/0028853 A1 | 3/2002 | Manzer et al. | 518/713 |
| 2002/0048541 A1 | 4/2002 | Schodel et al. | 422/198 |
| 2002/0188031 A1 | 12/2002 | Kibby | 518/715 |
| 2003/0083390 A1 | 5/2003 | Shah et al. | |
| 2003/0105171 A1 | 6/2003 | Subramanian et al. | 518/715 |
| 2003/0116503 A1 | 6/2003 | Wang et al. | 210/660 |
| 2003/0185721 A1 | 10/2003 | Wang et al. | 422/177 |
| 2003/0219903 A1 | 11/2003 | Wang et al. | 436/37 |
| 2004/0104010 A1 | 6/2004 | Kenny et al. | 165/80.4 |
| 2004/0107831 A1 | 6/2004 | Graham et al. | 95/96 |
| 2004/0123626 A1 | 7/2004 | Caze et al. | 65/17.2 |
| 2004/0125689 A1 | 7/2004 | Ehrfeld et al. | 366/165.1 |
| 2004/0127352 A1 | 7/2004 | Jin et al. | 502/322 |
| 2004/0130057 A1 | 7/2004 | Mehrabi et al. | 264/171.13 |
| 2004/0131345 A1 | 7/2004 | Kylberg et al. | 392/465 |
| 2004/0131507 A1 | 7/2004 | Saitmacher et al. | 422/111 |
| 2004/0131829 A1 | 7/2004 | Joseph et al. | 428/166 |
| 2004/0132832 A1 | 7/2004 | Espinoza et al. | 518/716 |
| 2004/0136902 A1 | 7/2004 | Plath et al. | 423/651 |
| 2004/0141893 A1 | 7/2004 | Martin | 422/198 |
| 2004/0143059 A1 | 7/2004 | Cabrera | 524/800 |
| 2004/0144421 A1 | 7/2004 | Parce et al. | 137/14 |
| 2004/0156762 A1 | 8/2004 | Schuppich et al. | 422/191 |
| 2005/0165121 A1* | 7/2005 | Wang | B01J 19/0093 518/726 |
| 2007/0017633 A1 | 1/2007 | Tonkovich | 156/300 |
| 2008/0058434 A1 | 3/2008 | Tonkovich et al. | 518/704 |
| 2009/0293359 A1 | 12/2009 | Simmons et al. | |
| 2009/0305881 A1 | 12/2009 | Sietsma et al. | 502/259 |
| 2011/0028575 A1 | 2/2011 | Van De Loosdrecht et al. | |
| 2011/0240288 A1 | 10/2011 | Kibby | 166/267 |
| 2014/0045953 A1* | 2/2014 | Daly | B01J 23/8913 518/714 |
| 2014/0088206 A1* | 3/2014 | Daly | B01J 21/063 518/715 |
| 2015/0018439 A1* | 1/2015 | Daly | B01J 37/18 518/728 |

(56) References Cited

U.S. PATENT DOCUMENTS

2015/0202613 A1* 7/2015 Richard .............. B01J 23/8913
 518/712

FOREIGN PATENT DOCUMENTS

| | | |
|---|---|---|
| DE | 3926466 | 2/1991 |
| EP | 1 311 341 B1 | 8/2001 |
| EP | 0 904 608 B1 | 12/2001 |
| EP | 1 362 634 A1 | 11/2003 |
| EP | 1102628 | 11/2006 |
| GB | 1531134 | 11/1978 |
| GB | 2077136 | 12/1981 |
| JP | 2002501430 | 1/2002 |
| JP | 2002126498 | 5/2002 |
| WF | 01/54807 A1 | 2/2001 |
| WO | 9421372 | 9/1994 |
| WO | 9700442 | 1/1997 |
| WO | 97/32687 | 12/1997 |
| WO | 9828073 | 7/1998 |
| WO | 9838147 | 9/1998 |
| WO | 98/55812 | 10/1998 |
| WO | 9916542 | 4/1999 |
| WO | 0006301 | 2/2000 |
| WO | 00/06295 | 10/2000 |
| WO | 01/10773 A1 | 2/2001 |
| WO | 01/12312 A2 | 2/2001 |
| WO | 01/12753 A1 | 2/2001 |
| WO | 01/95237 A2 | 12/2001 |
| WO | 0196015 | 12/2001 |
| WO | 02/064248 | 8/2002 |
| WO | 02064248 | 8/2002 |
| WO | 03/006149 | 1/2003 |
| WO | 03/026788 | 4/2003 |
| WO | 03/078052 A1 | 9/2003 |
| WO | 03078052 | 9/2003 |
| WO | 03/099429 | 12/2003 |
| WO | 03/106386 A2 | 12/2003 |
| WO | 2004/045760 | 6/2004 |
| WO | 2004/050799 | 6/2004 |
| WO | 2004/052518 | 6/2004 |
| WO | 2004/052530 | 6/2004 |
| WO | 2004/052941 | 6/2004 |
| WO | 2004/054013 | 6/2004 |
| WO | 2004/054696 | 7/2004 |
| WO | 2004/062790 | 7/2004 |
| WO | 2004/062791 | 7/2004 |
| WO | 2004/062792 | 7/2004 |
| WO | 2004/067160 | 8/2004 |
| WO | 2004/067444 | 8/2004 |
| WO | 2004/067492 | 8/2004 |
| WO | 2004/067708 | 8/2004 |
| WO | 2008104793 | 9/2008 |
| WO | 2012107718 | 8/2012 |
| ZA | 855317 | 7/1985 |

OTHER PUBLICATIONS

International Preliminary Report on Patentability, Application No. PCT/US2013/059142, mailed Oct. 21, 2014.
International Search Report and Written Opinion, Application No. PCT/US2013/059142, mailed Jan. 7, 2014.
Hinchiranan et al.; "TiO2 promoted Co/SiO2 catalysts for Fischer-Tropsch synthesis"; Fuel Processing Technology, 89 (2008).
Berge et al.; "XANES study of the susceptibility of nano-sized cobalt crystallites to oxidation during realistic Fischer-Tropsch synthesis"; Applied Catalysis A: General 312 (2006) 12-19.
Oyvind Borg; "Role of Alumina Support in Cobalt Fischer-Tropsch Synthesis"; Thesis for the degree of doktor ingenior; Norwegian University of Science and Technology; Apr. 2007
Moodley; "On the Deactivation of Cobalt-based Fischer-Tropsch Synthesis Catalysts"; 2008.
Kraum; "Fischer-Tropsch Syn thesis on Supported Cobalt-Based Catalysts: Influence of Various Preparation Methods and Supports on Catalyst Activity and Chain Growth Probability"; Thesis; Oct. 1999.
Korean Office Action, Application No. 2015-7003326, issued Sep. 24, 2015. No English language translation.
European Communication Pursuant to Article 94(3) EPC, Application No. 13 770 559.6, dated Jan. 13, 2016.
Notice of Allowance, Canadian Application No. 2,880,199, dated Sep. 11, 2013.

* cited by examiner

FISCHER-TROPSCH PROCESS

This is a continuation under 35 U.S.C. §120 of U.S. application Ser. No. 13/802,921, filed Mar. 14, 2013. Priority is claimed under 35 U.S.C. §119(e) to U.S. Provisional Application 61/716,772 filed Oct. 22, 2012. Priority is also claimed under 35 U.S.C. §119(d) to United Kingdom Patent Application No. 1214122.2, filed Aug. 7, 2012. These applications are incorporated herein by reference.

TECHNICAL FIELD

This invention relates to a Fischer-Tropsch process, and more particularly, to a Fischer-Tropsch process that is conducted in a microchannel reactor.

BACKGROUND

The Fischer-Tropsch reaction involves converting a reactant comprising $H_2$ and CO in the presence of a catalyst to one or more hydrocarbon products.

SUMMARY

This invention relates to a process for conducting a Fischer-Tropsch reaction, comprising: flowing a reactant mixture in a microchannel reactor in contact with a catalyst to form a product comprising at least one higher molecular weight hydrocarbon product; the catalyst being derived from a catalyst precursor comprising cobalt, a promoter such as Pd, Pt, Rh, Ru, Re, Ir, Au, Ag and/or Os, and a surface modified support, wherein the surface of the support is modified by being treated with silica, titania, zirconia, magnesia, chromia, alumina, or a mixture of two or more thereof; wherein the product further comprises a tail gas, at least part of the tail gas being separated from the higher molecular weight hydrocarbon product and combined with fresh synthesis gas to form the reactant mixture, the volumetric ratio of the fresh synthesis gas to the tail gas in the reactant mixture being in the range from about 1:1 to about 10:1, or from about 1:1 to about 8:1, or from about 1:1 to about 6:1, or from about 1:1 to about 4:1, or from about 3:2 to about 7:3, or about 2:1; the reactant mixture comprising $H_2$ and CO, the mole ratio of $H_2$ to CO in the reactant mixture based on the concentration of CO in the fresh synthesis gas being in the range from about 1.4:1 to about 2:1 or from about 1.5:1 to about 2.1:1, or from about 1.6:1 to about 2:1, or from about 1.7:1 to 1.9:1; wherein the conversion of CO for the fresh synthesis gas in the reactant mixture is at least about 70%, or at least about 75%, or at least about 80%, or at least about 85%, or at least about 90%; and the selectivity to methane in the product is in the range from about 0.01 to 10%, or from about 1% to about 10%, or from about 1% to about 5%, or from about 3% to about 9%, or from about 4% to about 8%.

The one-pass conversion of CO for the CO in the reactant mixture (i.e., CO from the fresh synthesis gas plus CO from the tail gas that is combined with the fresh synthesis gas) may be in the range from about 70% to about 90%, or from about 70% to about 85%, or from about 70% to about 80%.

The CO conversion for the CO in fresh synthesis gas may be in the range from about 88% to about 95%, or from about 90% to about 94%, or from about 91 to about 93%.

The support may comprise a refractory metal oxide, carbide, carbon, nitride, or mixture of two or more thereof. The support may comprise alumina, zirconia, silica, titania, or a mixture of two or more thereof.

The support may comprise a $TiO_2$ modified silica support wherein the support contains at least about 11% by weight $TiO_2$, or from about 11% to about 30% by weight $TiO_2$, or from about 15 to about 17% by weight $TiO_2$, or about 16% by weight $TiO_2$.

The surface of the surface modified support may be amorphous.

The catalyst precursor may comprise a cobalt oxide. The cobalt oxide may comprise $Co_3O_4$.

The microchannel reactor may comprise at least one process microchannel in thermal contact with a heat exchanger, the catalyst being in the process microchannel.

The microchannel reactor may comprise a plurality of process microchannels and a plurality of heat exchange channels, the catalyst being in the process microchannels.

The microchannel reactor may comprise a plurality of process microchannels and a plurality of heat exchange channels, the catalyst being in the process microchannels, each heat exchange channel being in thermal contact with at least one process microchannel, at least one manifold for flowing the reactant mixture into the process microchannels, at least one manifold for flowing product out of the process microchannels, at least one manifold for flowing a heat exchange fluid into the heat exchange channels, and at least one manifold for flowing the heat exchange fluid out of the heat exchange channels.

A plurality of the microchannel reactors may be positioned in a vessel, each microchannel reactor comprising a plurality of process microchannels and a plurality of heat exchange channels, the catalyst being in the process microchannels, each heat exchange channel being in thermal contact with at least one process microchannel, the vessel being equipped with a manifold for flowing the reactant mixture to the process microchannels, a manifold for flowing the product from the process microchannels, a manifold for flowing a heat exchange fluid to the heat exchange channels, and a manifold for flowing the heat exchange fluid from the heat exchange channels.

The catalyst may be in the form of particulate solids. The microchannel reactor comprises one or more process microchannels, and the catalyst may be coated on interior walls of the process microchannels or grown on interior walls of the process microchannels. The catalyst may be supported on a support having a flow-by configuration, a flow-through configuration, or a serpentine configuration. The catalyst may be supported on a support having the configuration of a foam, felt, wad, fin, or a combination of two or more thereof.

The higher molecular weight aliphatic hydrocarbon product may comprise one or more hydrocarbons boiling at a temperature of at least about 30° C. at atmospheric pressure. The higher molecular weight aliphatic hydrocarbon product may comprise one or more hydrocarbons boiling above a temperature of about 175° C. at atmospheric pressure. The higher molecular weight aliphatic hydrocarbon product may comprise one or more paraffins and/or one or more olefins of about 5 to about 100 carbon atoms. The higher molecular weight aliphatic hydrocarbon product may comprise one or more olefins, one or more normal paraffins, one or more isoparaffins, or a mixture of two or more thereof. The higher molecular weight aliphatic hydrocarbon product may be further processed using separation, fractionation, hydrocracking, hydroisomerizing, dewaxing, or a combination of two or more thereof. The higher molecular weight aliphatic hydrocarbon product may be further processed to form an oil of lubricating viscosity or a middle distillate fuel. The higher molecular weight aliphatic hydrocarbon product may be further processed to form a fuel.

The microchannel reactor may comprise at least one process microchannel and at least one heat exchanger, the heat exchanger comprising at least one heat exchange channel in thermal contact with the at least one process microchannel, the process microchannel having fluid flowing in it in one direction, the heat exchange channel having fluid flow in a direction that is co-current, counter-current or cross-current to the flow of fluid in the process microchannel.

The microchannel reactor may comprise at least one process microchannel and at least one heat exchanger, a tailored heat exchange profile being provided along the length of the process microchannel, the local release of heat given off by the reaction conducted in the process microchannel being matched with cooling provided by the heat exchanger.

The microchannel reactor may comprise a plurality of process microchannels, the process microchannels being formed by positioning a waveform between planar sheets. The microchannel reactor may further comprises a plurality of heat exchange channels in thermal contact with the process microchannels, the heat exchange channels being formed by positioning a waveform between planar sheets.

The microchannel reactor may comprise a plurality of plates in a stack defining a plurality of Fischer-Tropsch process layers and a plurality of heat exchange layers, each plate having a peripheral edge, the peripheral edge of each plate being welded to the peripheral edge of the next adjacent plate to provide a perimeter seal for the stack.

The deactivation rate of the catalyst may be less than a loss of about 0.2% CO conversion per day.

The product may comprise a higher molecular weight hydrocarbon product, $H_2O$ and $H_2$, the $H_2O$ partial pressure for the product being in the range from about 3 to about 10 bar, the $H_2O/H_2$ molar ratio for the product being in the range from about 1:1 to about 5:1, and the conversion of CO based on the total reactant mixture fed to the reactor (i.e., the sum of fresh synthesis gas and recycle tail gas) being in the range from about 70 to about 80%, or about 70 to about 85%, or from about 80 to about 85%, or from about 82 to about 83%.

The present invention, in one embodiment, may provide the following combination of advantages and surprise results:

A) High overall CO conversion (in one embodiment about 90% or higher) in a single stage microchannel process;

B) Achieving (A) with, in one embodiment, a ratio of about 0.45 to about 0.50 tail gas recycle to fresh synthesis gas.

C) This allows for tolerating high CO conversions, which may provide for high water partial pressures and high water to hydrogen ratios. Generally cobalt catalysts may be expected to deactivate rapidly under these conditions.

D) Operating a substoichiometric $H_2/CO$ ratios (that is $H_2/CO$ ratios lower than the stoichiometric consumption ratio, which may be about 2.12). In one embodiment, the tail gas $H_2/CO$ ratio may be less than about 1.0, which is lower than typical cobalt FT catalysts may be capable of operating. Generally cobalt catalysts may deactivate rapidly under these conditions.

E) Achieving these results at both: (1) relatively low operating temperatures (in one embodiment, about 200-210° C.), and (2) employing a high reaction rate (in one embodiment, catalyst productivities generally at or above 2,000 v/v/hr and just about 1 gm C5+/gm catalyst/hour or higher).

F) Achieving low methane (and other light gas) selectivities which means high $C_5+$ liquid selectivities (e.g., in one embodiment about 90% or higher).

A problem in the art relates to the fact that in order to achieve relatively high conversions of CO it is often necessary to employ two stage Fischer-Tropsch reactors. This leads to waste and expense. With the present invention, on the other hand, it is possible to achieve relatively high levels of CO conversion with a single stage reactor at relatively low recycle ratios due to the fact that at least part of the tail gas produced during the Fischer-Tropsch process is recycled back to the reactor where it is combined with fresh synthesis gas, and relatively high per pass (total reactor feed) CO conversions can be achieved without accelerated catalyst deactivation. The ratio of recycled tail gas to fresh synthesis gas in the reactant mixture may be about 0.8 or higher.

BRIEF DESCRIPTION OF THE DRAWINGS

In the annexed drawings like parts and features have like references. A number of the drawings are schematic illustrations which may not necessarily be drawn to scale.

FIGS. 10-12 are schematic illustrations of fin assemblies that may be used for supporting the catalyst.

DETAILED DESCRIPTION

Figure 1:
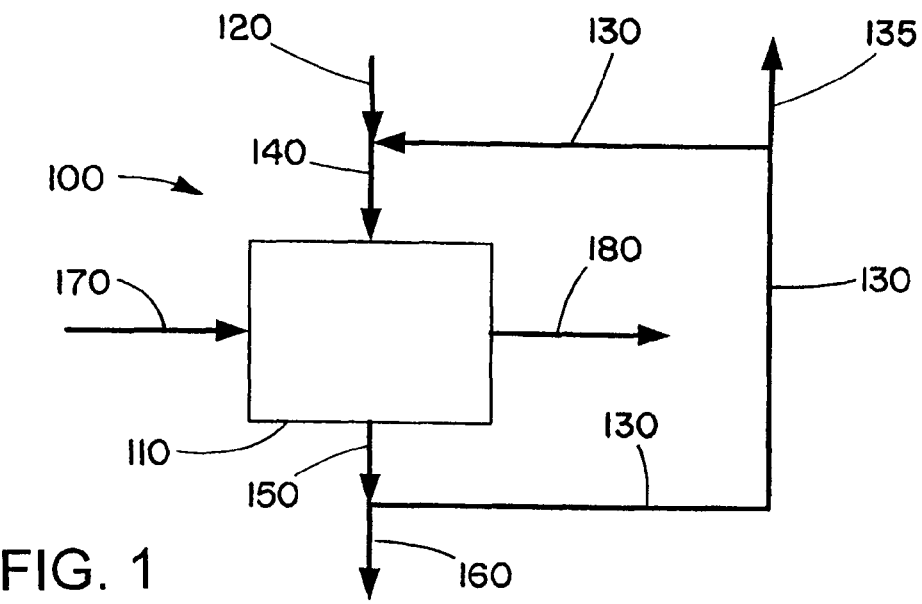
FIG. 1 is a flow sheet illustrating the inventive process in a particular form, the process comprising converting a reactant mixture comprising fresh synthesis gas and recycled tail gas to one or more higher molecular weight hydrocarbons in a microchannel reactor.

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The transitional words or phrases, such as "comprising," "including," "carrying," "having," "containing," "involving," "holding," and the like, are to be understood to be open-ended, i.e., to mean including but not limited to.

The term "microchannel" refers to a channel having at least one internal dimension of height or width of up to about 10 millimeters (mm), and in one embodiment up to about 5 mm, and in one embodiment up to about 2 mm, and in one embodiment up to about 1 mm. The microchannel may comprise at least one inlet and at least one outlet wherein the at least one inlet is distinct from the at least one outlet. The microchannel may not be merely an orifice. The microchannel may not be merely a channel through a zeolite or a mesoporous material. The length of the microchannel may be at least about two times the height or width, and in one embodiment at least about five times the height or width, and in one embodiment at least about ten times the height or width. The internal height or width of the microchannel may be in the range of about 0.05 to about 10 mm, or from about 0.05 to about 5 mm, or from about 0.05 to about 2 mm, or from about 0.05 to about 1.5 mm, or from about 0.05 to about 1 mm, or from about 0.05 to about 0.75 mm, or from about 0.05 to about 0.5 mm, or from about 1 to about 10 mm, or from about 2 to about 8 mm, or from about 3 to about 7 mm. The other internal dimension of height or width may be of any dimension, for example, up to about 3 meters, or about 0.01 to about 3 meters, and in one embodiment about 0.1 to about 3 meters, or about 1 to about 10 mm, or from about 2 to about 8 mm, or from about 3 to about 7 mm. The length of the microchannel may be of any dimension, for example, up to about 10 meters, and in one embodiment from about 0.1 to about 10 meters, and in one embodiment from about 0.2 to about 10 meters, and in one embodiment from about 0.2 to about 6 meters, and in one embodiment from 0.2 to about 3 meters. The microchannel may have a cross section having any shape, for example, a square, rectangle, circle, semi-circle, trapezoid, etc. The shape and/or size of the cross section of the microchannel may vary over its length. For example, the height or width may taper from a relatively large dimension to a relatively small dimension, or vice versa, over the length of the microchannel.

The term "microchannel reactor" refers to an apparatus comprising one or more process microchannels wherein a reaction process is conducted. The process may be a Fischer-Tropsch reaction process. The microchannel reactor may comprise one or more slots for receiving one or more catalyst inserts (e.g., one or more fins or fin assemblies, one or more corrugated inserts, etc.) wherein the process microchannels comprise the slots, are positioned in the catalyst inserts, and/or comprise openings formed by the walls of the slots and the inserts. When two or more process microchannels are used, the process microchannels may be operated in parallel. The microchannel reactor may include a header or manifold assembly for providing for the flow of fluid into the one or more process microchannels, and a footer or manifold assembly providing for the flow of fluid out of the one or more process microchannels. The microchannel reactor may comprise one or more heat exchange channels adjacent to and/or in thermal contact with the one or more process microchannels. The heat exchange channels may provide cooling for the fluids in the process microchannels. The heat exchange channels may be microchannels. The microchannel reactor may include a header or manifold assembly for providing for the flow of heat exchange fluid into the heat exchange channels, and a footer or manifold assembly providing for the flow of heat exchange fluid out of the heat exchange channels.

The term "process microchannel" refers to a microchannel wherein a process is conducted. The process may be a Fischer-Tropsch (FT) reaction process.

The term "volume" with respect to volume within a process microchannel may include all volume in the process microchannel a process fluid may flow through or flow by. This volume may include volume within surface features that may be positioned in the process microchannel and adapted for the flow of fluid in a flow-through manner or in a flow-by manner.

The term "adjacent" when referring to the position of one channel relative to the position of another channel may mean directly adjacent such that a wall or walls separate the two channels. In one embodiment, the two channels may have a common wall. The common wall may vary in thickness. However, "adjacent" channels may not be separated by an intervening channel that may interfere with heat transfer between the channels. One channel may be adjacent to another channel over only part of the dimension of the another channel. For example, a process microchannel may be longer than and extend beyond one or more adjacent heat exchange channels.

The term "thermal contact" refers to two bodies, for example, two channels, that may or may not be in physical contact with each other or adjacent to each other but still exchange heat with each other. One body in thermal contact with another body may heat or cool the other body.

The term "fluid" refers to a gas, a liquid, a mixture of a gas and a liquid, or a gas or a liquid containing dispersed solids, liquid droplets and/or gaseous bubbles. The droplets and/or bubbles may be irregularly or regularly shaped and may be of similar or different sizes.

The terms "gas" and "vapor" may have the same meaning and are sometimes used interchangeably.

The term "residence time" or "average residence time" refers to the internal volume of a space within a channel occupied by a fluid flowing in the space divided by the average volumetric flow rate for the fluid flowing in the space at the temperature and pressure being used.

The terms "upstream" and "downstream" refer to positions within a channel (e.g., a process microchannel) or in a process flow sheet that is relative to the direction of flow of a fluid in the channel or process flow sheet. For example, a position within a channel or process flow sheet not yet reached by a portion of a fluid stream flowing toward that position would be downstream of that portion of the fluid stream. A position within the channel or process flow sheet already passed by a portion of a fluid stream flowing away from that position would be upstream of that portion of the fluid stream. The terms "upstream" and "downstream" do not necessarily refer to a vertical position since the channels used herein may be oriented horizontally, vertically or at an inclined angle.

The term "plate" refers to a planar or substantially planar sheet or plate. the plate may be referred to as a shim. The thickness of the plate may be the smallest dimension of the plate and may be up to about 4 mm, or in the range from about 0.05 to about 2 mm, or in the range of about 0.05 to about 1 mm, or in the range from about 0.05 to about 0.5 mm. The plate may have any length and width.

The term "surface feature" refers to a depression in a channel wall and/or a projection from a channel wall that disrupts flow within the channel. The surface features may be in the form of circles, spheres, frustrums, oblongs, squares, rectangles, angled rectangles, checks, chevrons, vanes, airfoils, wavy shapes, and the like, and combinations of two or more thereof. The surface features may contain subfeatures where the major walls of the surface features further contain smaller surface features that may take the form of notches, waves, indents, holes, burrs, checks, scallops, and the like. The surface features may have a depth, a width, and for non-circular surface features a length. The surface features may be formed on or in one or more of the interior walls of the process microchannels, heat exchange channels and/or combustion channels used in accordance with the disclosed process. The surface features may be referred to as passive surface features or passive mixing features. The surface features may be used to disrupt flow (for example, disrupt laminar flow streamlines) and create advective flow at an angle to the bulk flow direction.

The term "heat exchange channel" refers to a channel having a heat exchange fluid in it that provides heat and/or absorbs heat. The heat exchange channel may absorb heat from or provide heat to an adjacent channel (e.g., process microchannel) and/or one or more channels in thermal contact with the heat exchange channel. The heat exchange channel may absorb heat from or provide heat to channels that are adjacent to each other but not adjacent to the heat exchange channel. In one embodiment, one, two, three or more channels may be adjacent to each other and positioned between two heat exchange channels.

The term "heat transfer wall" refers to a common wall between a process microchannel and an adjacent heat exchange channel where heat transfers from one channel to the other through the common wall.

The term "heat exchange fluid" refers to a fluid that may give off heat and/or absorb heat.

The term "waveform" refers to a contiguous piece of material (e.g., a thermally conductive material) that is transformed from a planar object to a three-dimensional object. The waveform may be used to form one or more microchannels. The waveform may comprise a right angled corrugated insert which may be sandwiched between opposed planar sheets or shims. The right angled corrugated insert may have rounded edges. In this manner one or more microchannels may be defined on three sides by the waveform and on the fourth side by one of the planar sheets or shims. The waveform may be made of any of the materials disclosed herein as being useful for making the microchannel reactor. These may include copper, aluminum, stainless steel, and the like. The thermal conductivity of the waveform may be about 1 W/m-K or higher.

The term "bulk flow direction" may refer to the vector through which fluid may travel in an open path in a channel.

The term "bulk flow region" may refer to open areas within a microchannel. A contiguous bulk flow region may allow rapid fluid flow through a microchannel without significant pressure drops. In one embodiment, the flow in the bulk flow region may be laminar. A bulk flow region may comprise at least about 5% of the internal volume and/or cross-sectional area of a microchannel, or from about 5% to about 100%, or from about 5% to about 99%, or from about 5% to about 95%, or from about 5% to about 90%, or from about 30% to about 80% of the internal volume and/or cross-sectional area of the microchannel.

The terms "open channel" or "flow-by channel" or "open path" refers to a channel (e.g., a microchannel) with a gap of at least about 0.01 mm that extends all the way through the channel such that fluid may flow through the channel without encountering a barrier to flow. The gap may extend up to about 10 mm.

The term "cross-sectional area" of a channel (e.g., process microchannel) refers to an area measured perpendicular to the direction of the bulk flow of fluid in the channel and may include all areas within the channel including any surface features that may be present, but does not include the channel walls. For channels that curve along their length, the cross-sectional area may be measured perpendicular to the direction of bulk flow at a selected point along a line that parallels the length and is at the center (by area) of the channel. Dimensions of height and width may be measured from one channel wall to the opposite channel wall. These dimensions may not be changed by application of a coating to the surface of the wall. These dimensions may be average values that account for variations caused by surface features, surface roughness, and the like.

The term "open cross-sectional area" of a channel (e.g., process microchannel) refers to an area open for bulk fluid flow in a channel measured perpendicular to the direction of the bulk flow of fluid flow in the channel. The open cross-sectional area may not include internal obstructions such as surface features and the like which may be present.

The term "superficial velocity" for the velocity of a fluid flowing in a channel refers to the velocity resulting from dividing the volumetric flow rate of the fluid at the inlet temperature and pressure of the channel by the cross-sectional area of the channel.

The term "free stream velocity" refers to the velocity of a stream flowing in a channel at a sufficient distance from the sidewall of the channel such that the velocity is at a maximum value. The velocity of a stream flowing in a channel is zero at the sidewall if a no slip boundary condition is applicable, but increases as the distance from the sidewall increases until a constant value is achieved. This constant value is the "free stream velocity."

The term "process fluid" is used herein to refer to reactants, product and any diluent or other fluid that may flow in a process microchannel.

The term "reaction zone" refers to the space within a microchannel wherein a chemical reaction occurs or wherein a chemical conversion of at least one species occurs. The reaction zone may contain one or more catalysts.

The term "contact time" refers to the volume of a reaction zone within a microchannel divided by the volumetric feed flow rate of the reactants at a temperature of 0° C. and a pressure of one atmosphere.

The term "fresh synthesis gas" refers to synthesis gas that flows into a microchannel reactor and is used as a reactant in a Fischer-Tropsch reaction.

The term "tail gas" refers to a gaseous product produced during a Fisher-Tropsch reaction. The tail gas may contain CO and $H_2$.

The term "reactant mixture" refers to a mixture of fresh synthesis gas, and a tail gas or tail gas components (e.g., CO and $H_2$) recycled from the Fischer-Tropsch reaction.

The term "conversion of CO" refers to the CO mole change between the fresh synthesis gas in the reactant mixture and product, divided by the moles of CO in the fresh synthesis gas.

The term "one-pass conversion of CO" refers to the conversion of CO from the overall reactant mixtures (i.e., fresh synthesis gas plus recycled tail gas or recycled tail gas components) after one pass through the microchannel reactor.

The term "selectivity to methane" refers to the moles of methane in the product minus the moles of methane in the reactant mixture, divided by moles of the CO that are consumed in the reaction.

The term "yield" refers to the number of moles of product exiting a microchannel reactor divided by the number of moles of a reactant entering the microchannel reactor.

The term "cycle" refers to a single pass of the reactants through a microchannel reactor.

The term "graded catalyst" refers to a catalyst with one or more gradients of catalytic activity. The graded catalyst may have a varying concentration or surface area of a catalytically active metal. The graded catalyst may have a varying turnover rate of catalytically active sites. The graded catalyst may have physical properties and/or a form that varies as a function of distance. For example, the graded catalyst may have an active metal concentration that is relatively low at the entrance to a process microchannel and increases to a higher concentration near the exit of the process microchannel, or vice versa; or a lower concentration of catalytically active metal nearer the center (i.e., midpoint) of a process microchannel and a higher concentration nearer a process microchannel wall, or vice versa, etc. The thermal conductivity of a graded catalyst may vary from one location to another within a process microchannel. The surface area of a graded catalyst may be varied by varying size of catalytically active metal sites on a constant surface area support, or by varying the surface area of the support such as by varying support type or particle size. A graded catalyst may have a porous support where the surface area to volume ratio of the support is higher or lower in different parts of the process microchannel followed by the application of the same catalyst coating everywhere. A combination of two or more of the preceding embodiments may be used. The graded catalyst may have a single catalytic component or multiple catalytic components (for example, a bimetallic or trimetallic catalyst). The graded catalyst may change its properties and/or composition gradually as a function of distance from one location to another within a process microchannel. The graded catalyst may comprise rimmed particles that have "eggshell" distributions of catalytically active metal within each particle. The graded catalyst may be graded in the axial direction along the length of a process microchannel or in the lateral direction. The graded catalyst may have different catalyst compositions, different loadings and/or numbers of active catalytic sites that may vary from one position to another position within a process microchannel. The number of catalytically active sites may be changed by altering the porosity of the catalyst structure. This may be accomplished using a washcoating process that deposits varying amounts of catalytic material. An example may be the use of different porous catalyst thicknesses along the process microchannel length, whereby a thicker porous structure may be left where more activity is required. A change in porosity for a fixed or variable porous catalyst thickness may also be used. A first pore size may be used adjacent to an open area or gap for flow and at least one second pore size may be used adjacent to the process microchannel wall.

The term "chain growth" refers to the growth in a molecule resulting from a reaction in which the molecule grows with the addition of new molecular structures (e.g., the addition of methylene groups to a hydrocarbon chain in a Fischer-Tropsch synthesis).

The term "aliphatic hydrocarbon" refers to aliphatic compounds, such as alkanes, alkenes, alkynes, and the like.

The term "higher molecular weight aliphatic hydrocarbon" refers to an aliphatic hydrocarbon having 2 or more carbon atoms, or 3 or more carbon atoms, or 4 or more carbon atoms, or 5 or more carbon atoms, or 6 or more carbon atoms. The higher molecular weight aliphatic hydrocarbons may have up to about 200 carbon atoms or higher, or up to about 150 carbon atoms, or up to about 100 carbon atoms, or up to about 90 carbon atoms, or up to about 80 carbon atoms, or up to about 70 carbon atoms, or up to about 60 carbon atoms, or up to about 50 carbon atoms, or up to about 40 carbon atoms, or up to about 30 carbon atoms. Examples may include ethane, propane, butane, pentane, hexane, octane, decane, dodecane, and the like.

The term "Fischer-Tropsch" or "FT" refers to a chemical reaction represented by the equation:

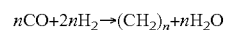

$$nCO + 2nH_2 \rightarrow (CH_2)_n + nH_2O$$

This reaction is an exothermic reaction. n may be any number, for example from 1 to about 1000, or from about 2 to about 200, or from about 5 to about 150.

The term "Fischer-Tropsch product" or "FT product" refers to a hydrocarbon product made by a Fischer-Tropsch process. The FT liquid product may have a boiling point at or above about 30° C. at atmospheric pressure.

The term "FT tail gas" or "tail gas" refers to a gaseous product made by a Fischer-Tropsch process. The tail gas may have a boiling point below about 30° C. at atmospheric pressure. The tail gas may contain $H_2$ and CO.

The term "Co loading" may refer to the weight of Co in a catalyst divided by the total weight of the catalyst, that is, the total weight of the Co plus any co-catalyst or promoter as well as any support. If the catalyst is supported on an engineered support structure such as a foam, felt, wad or fin, the weight of such engineered support structure may not be included in the calculation. Similarly, if the catalyst is adhered to a channel wall, the weight of the channel wall may is not be included in the calculation.

The term "mm" may refer to millimeter. The term "nm" may refer to nanometer. The term "ms" may refer to millisecond. The term "µs" may refer to microsecond. The term "µm" may refer to micron or micrometer. The terms "micron" and "micrometer" have the same meaning and may be used interchangeably.

Unless otherwise indicated, all pressures are expressed in terms of absolute pressure.

The Process

The term "fresh synthesis gas" refers to a gaseous mixture that contains CO and $H_2$ and is not part of the recycled tail gas that is used during the inventive process. Synthesis gas may be referred to as syngas. During the inventive process, the fresh synthesis gas is combined with recycled tail gas, which also contains $H_2$ and CO, to form the reactant mixture used with the inventive process. The reactant mixture may comprise $H_2$ and CO with a molar ratio of $H_2$ to CO that may be in the range from about 1.4:1 to about 2.1:1, or from about 1.5:1 to about 2:1:1, or from about 1.6:1 to about 2:1, or from about 1.7:1 to about 1.9:1. The fresh synthesis gas may comprise $H_2$ and CO with the molar ratio of $H_2$ to CO being in the range from about 1.9:1 to about 2.1:1, or from about 1.95:1 to about 2.05:1, or from about 1.98:1 to about 2.02:1. The tail gas that is generated during the inventive process and combined with the fresh synthesis gas to form the reactant mixture may be referred to as recycled tail gas. The recycled tail gas may comprise $H_2$ and CO with a molar ratio of $H_2$ to CO in the range from about 0.5:1 to about 2:1, or from about 0.6:1 to about 1.8:1, or from about 0.7:1 to about 1.2:1. The volumetric ratio of the fresh synthesis gas to the tail gas in the reactant mixture may be in the range from about 1:1 to about 10:1, or from about 1:1 to about 8:1, or from about 1:1 to about 6:1, or from about 1:1 to about 4:1, or from about 3:2 to about 7:3, or about 2:1.

The inventive process, in its illustrated embodiments, will be initially described with respect to FIG. 1. Referring to FIG. 1, the process 100 employs the use of microchannel reactor 110. The microchannel reactor 110 may be referred to as a Fischer-Tropsch microchannel reactor. In operation fresh synthesis gas 120 is combined with recycled tail gas 130 to form reactant mixture 140. The fresh synthesis gas may be combined with the recycled tail gas upstream of the microchannel reactor 110, as shown in FIG. 1, or in the microchannel reactor 110.

In the microchannel reactor 100, the reactant mixture flows through one or more process microchannels in contact with a catalyst to form the product. The catalyst may be referred to as a Fischer-Tropsch catalyst and the product formed by contacting the Fischer-Tropsch catalyst may comprise one or more higher molecular weight aliphatic hydrocarbons as well as tail gas. The reaction is exothermic. The reaction may be controlled using a heat exchange fluid which flows through the microchannel reactor 110 as indicated by arrows 170 and 180. In an embodiment, the heat exchange fluid may comprise steam. The resulting product flows out of the microchannel reactor 110 as indicated by arrow 150. Tail gas is separated from the product, as indicated by arrow 130, and recycled to be combined with the fresh synthesis gas. Part of the tail gas may be separated from the process, as indicated by arrow 135, if it is desired to adjust the ratio of fresh synthesis gas to tail gas in the reactant mixture. With tail gas separated from the product, the remainder of the product, which comprises one or more higher molecular weight hydrocarbon products, and is indicated by arrow 160, is suitable for further processing.

Figure 2:
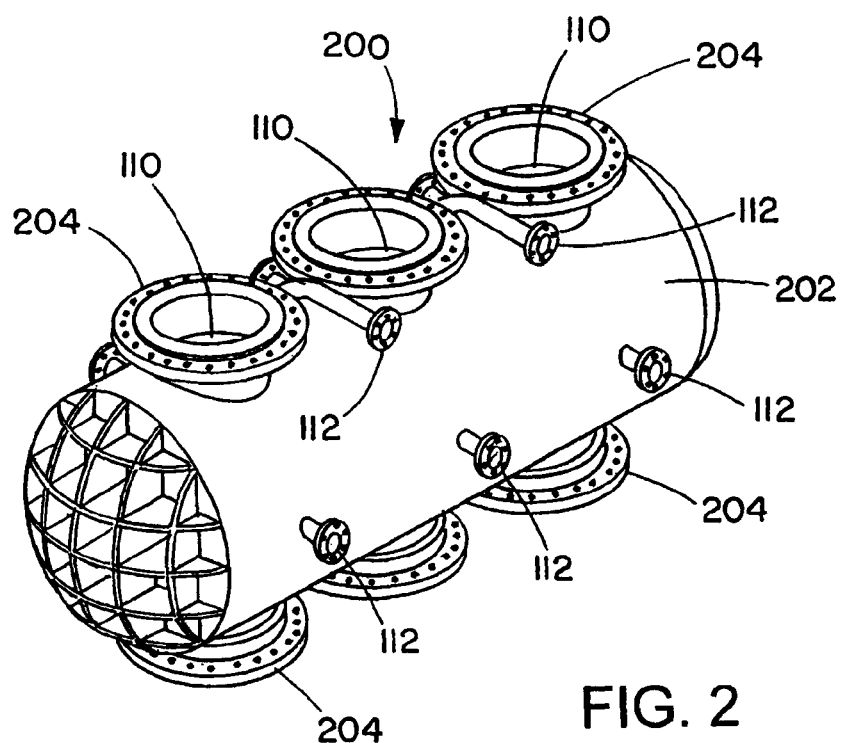
FIG. 2 is a schematic illustration of a vessel used for housing a plurality of the reactors.

One or more of the microchannel reactor cores 110 may be housed in vessel 200. Vessel 200 has the construction illustrated in FIG. 2. Referring to FIG. 2, the vessel 200 contains three Fischer-Tropsch microchannel reactor coress 110. Although three microchannel reactor coress are disclosed in the drawings, it will be understood that any desired number of microchannel reactor coress may be positioned in vessel 200. For example, the vessel 200 may contain from 1 to about 100 microchannel reactors 110, or from 1 to about 10, or from 1 to about 3 microchannel reactors 110. The vessel 200 may be a pressurizable vessel. The vessel 220 includes inlets and outlets 112 allowing for the flow of reactants into the microchannel reactors 110, product out of the microchannel reactors 110, and heat exchange fluid into and out of the microchannel reactors.

When the vessel 200 is used with the Fischer-Tropsch microchannel reactors 110, one of the inlets 112 is connected to a manifold which is provided for flowing the reactant mixture to Fischer-Tropsch process microchannels in the microchannel reactors 110. One of the inlets 112 is connected to a manifold which is provided for flowing heat exchange fluid (e.g., steam) to heat exchange channels in the microchannel reactors 110. One of the outlets 112 is connected to a manifold which provides for the flow of product from the Fischer-Tropsch process microchannels in the microchannel reactors 110. One of the outlets 112 is connected to a manifold to provide for the flow of the heat exchange fluid out of the heat exchange channels in the microchannel reactors 110.

The vessel 200 may be constructed using any suitable material sufficient for operating under the pressures and temperatures required for operating the Fischer-Tropsch microchannel reactors 110. For example, the shell 202 of the vessel 200 may be constructed of cast steel. The flanges 204, couplings and pipes may be constructed of 316 stainless steel. The vessel 200 may have any desired diameter, for example, from about 10 to about 1000 cm, or from about 50 to about 300 cm. The axial length of the vessel 200 may be of any desired value, for example, from about 0.5 to about 50 meters, or from about 1 to about 20 meters.

Figure 3:
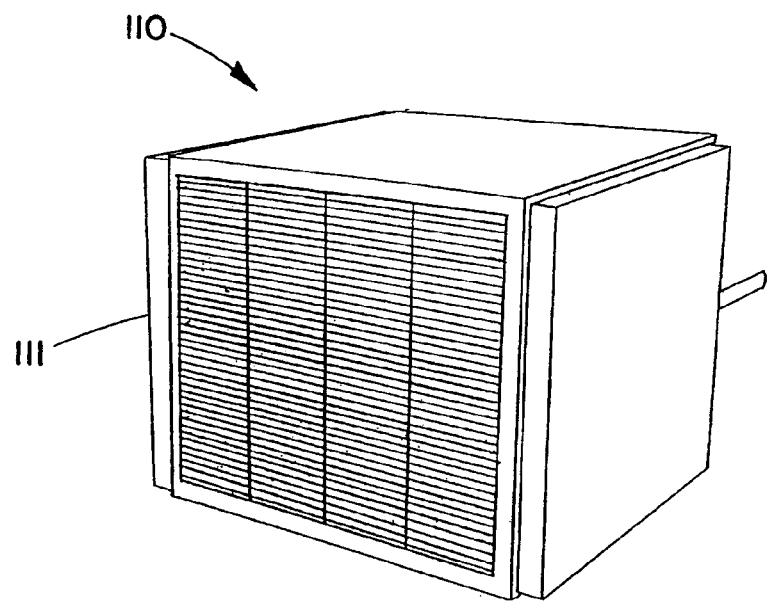
FIGS. 3 and 4 are illustrations of a reactor core for the microchannel reactor used with the inventive method.
Figure 4:
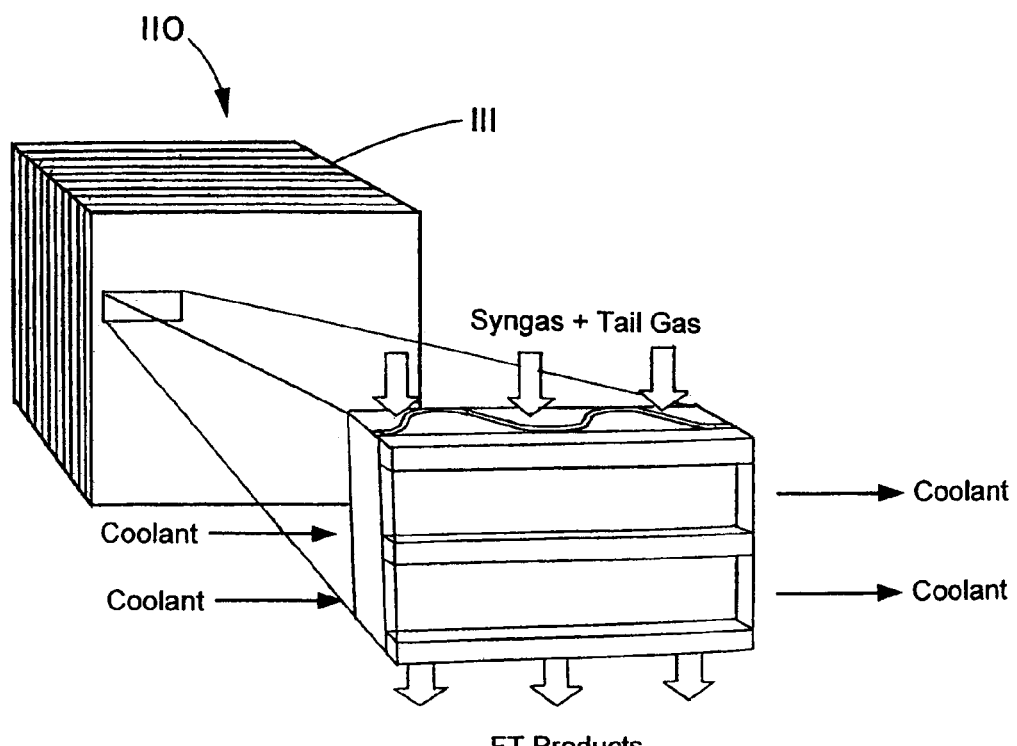

The microchannel reactors 110 may comprise a plurality of Fischer-Tropsch process microchannels and heat exchange channels stacked one above the other or positioned side-by-side. The microchannel reactors 110 may be in the form of cubic blocks. This is shown in FIGS. 3 and 4. These cubic blocks may be referred to as microchannel reactor cores 111. Each of the cubic blocks may have a length in the range from about 10 to about 1000 cm, or in the range from about 20 to about 200 cm. The width may be in the range from about 10 to about 1000 cm, or in the range from about 20 to about 200 cm. The height may be in the range from about 10 to about 1000 cm, or in the range from about 20 to about 200 cm.

The microchannel reactors 110 as well as the vessels 200 may be sufficiently small and compact so as to be readily transportable. As such, these reactors and vessels along with the other equipment used in the inventive process may be readily transported to remote locations, such as military bases, and the like. These reactors and vessels may be used on ships, oil drilling platforms, and the like.

The microchannel reactors 110 may contain a plurality of repeating units, each of which includes one or more Fischer-Tropsch process microchannels and one or more heat exchange channels. The repeating units that may be used include repeating units 210 and 210A illustrated in FIGS. 5 and 6, respectively. The microchannel reactor 110 may contain from 1 to about 1000 of the repeating units 230 or 230A, or from about 10 to about 500 of such repeating units. The catalyst used in the repeating units 210 and 210A may be in any form including beds of particulate solids and the various structured forms described below.

Figures 5, 6:
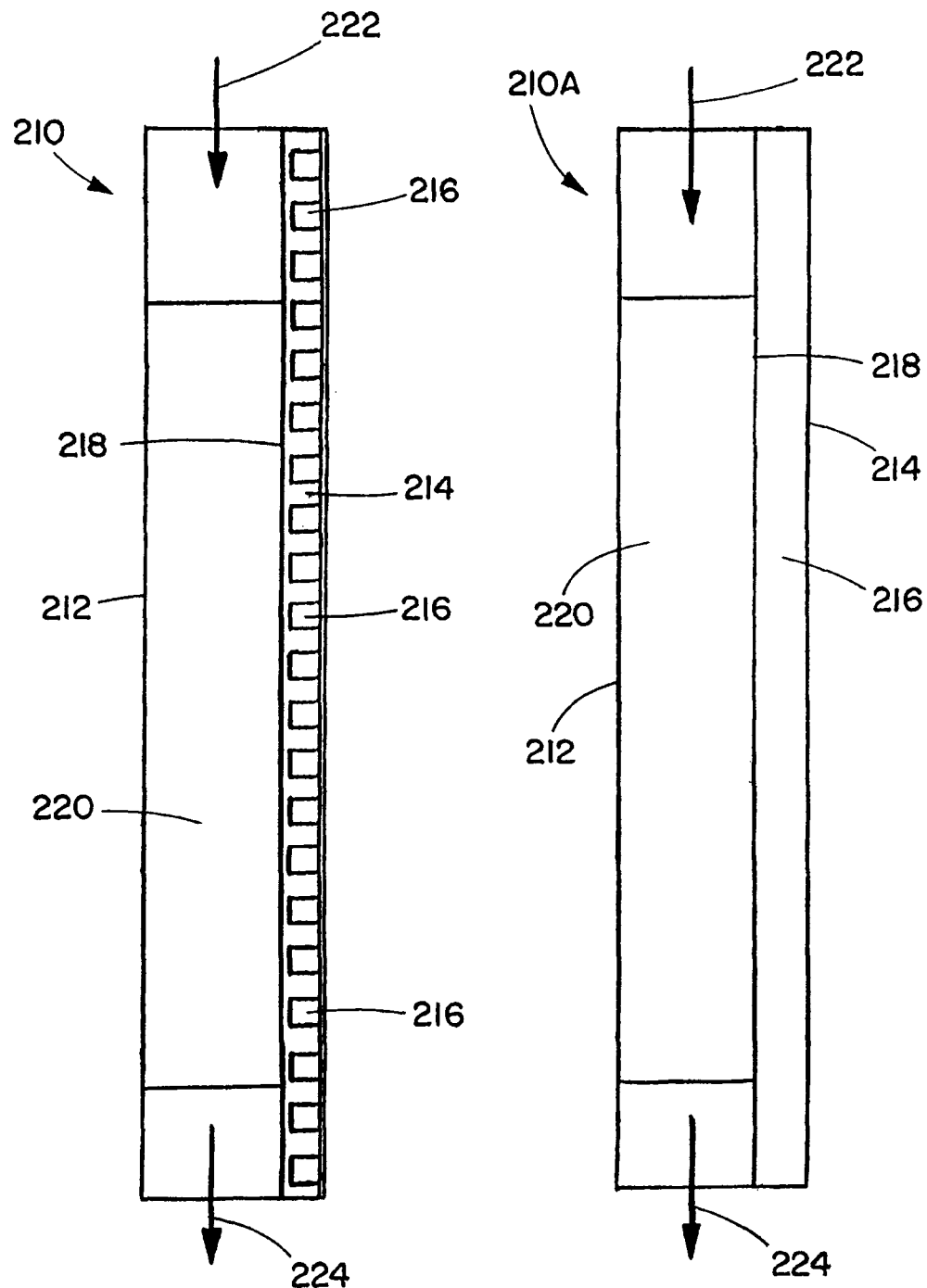
FIGS. 5 and 6 are schematic illustrations of repeating units that may be used in the microchannel reactor. Each of the repeating units illustrated in FIGS. 5 and 6 includes a Fischer-Tropsch process microchannel that includes a reaction zone containing a catalyst, and one or more adjacent heat exchange channels. Heat exchange fluid flowing in the heat exchange channels illustrated in FIG. 5 flows in a direction that is cross-current relative to the flow of process fluids in the process microchannel. Heat exchange fluid flowing in the heat exchange channel illustrated in FIG. 6 may flow in a direction that is co-current or counter-current to the flow of process fluid in the process microchannel. Tailored heat exchange profiles may be provided with each of these embodiments by controlling the number of heat exchange channels in thermal contact with different sections of the process microchannels. With these tailored heat exchange profiles more cooling channels may be provided in some parts of the process microchannels as compared to other parts of the process microchannels. For example, more cooling channels may be provided at or near the entrances to the reaction zones as compared to downstream parts of the reaction zones. The heat exchange profile may be tailored by controlling the flow rate of heat exchange fluid in the heat exchange channels. For example, a relatively high rate of flow of heat exchange fluid in the heat exchange channels in thermal contact with the entrances to the reaction zones may be used in combination with relatively low rates of flow of heat exchange fluid in heat exchange channels in thermal contact with downstream sections of the reaction zones.

Repeating unit 210 is illustrated in FIG. 5. Referring to FIG. 5, process microchannel 212 is positioned adjacent to heat exchange layer 214 which contains heat exchange channels 216. The heat exchange channels 216 may be microchannels. A common wall 218 separates the process microchannel 212 from the heat exchange layer 214. A catalyst is positioned in reaction zone 220 of the process microchannel 212. The reactant mixture (i.e., fresh synthesis gas and recycled tail gas) flows into the reaction zone 220 in process microchannel 212 in the direction indicated by arrow 222, contacts the catalyst in the reaction zone, and reacts to form the product. The product (i.e., one or more higher molecular weight aliphatic hydrocarbons and tail gas) flows out of the process microchannel 210 as indicated by arrow 224. Heat exchange fluid flows through the heat exchange channels 216 in a direction that is cross-current to the flow of reactant mixture and product in the process microchannel 212. The Fischer-Tropsch reaction conducted in the process microchannel 212 is exothermic and the heat exchange fluid provides cooling for the reaction.

Alternatively, the process microchannels and heat exchange channels may be aligned as provided for in repeating unit 210A. Repeating unit 210A, which is illustrated in FIG. 6, is identical to the repeating unit 210 illustrated in FIG. 5 with the exception that the heat exchange channels 216 are rotated 90° and the heat exchange fluid flowing through the heat exchange channels 216 flows in a direction that may be countercurrent to the flow of reactants and product in the process microchannel 212 or cocurrent relative to the direction of reactants and product in the process microchannel 212.

The process microchannels 212 may have cross sections having any shape, for example, square, rectangle, circle, semi-circle, etc. The internal height of each process microchannel 212 may be considered to be the smaller of the internal dimensions normal to the direction of flow of reactants and product through the process microchannel. Each of the process microchannels 212 may have an internal height of up to about 10 mm, or up to about 6 mm, or up to about 4 mm, or up to about 2 mm. The height may be in the range from about 0.05 to about 10 mm, or about 0.05 to about 6 mm, or about 0.05 to about 4 mm, or about 0.05 to about 2 mm. The width of each process microchannel 212 may be considered to be the other internal dimension normal to direction of flow of reactants and product through the process microchannel. The width of each process microchannel 212 may be of any dimension, for example, up to about 3 meters, or about 0.01 to about 3 meters, or about 0.1 to about 3 meters. The length of each process microchannel 210 may be of any dimension, for example, up to about 10 meters, or from about 0.1 to about 10 meters, or from about 0.2 to about 6 meters, or from about 0.2 to about 3 meters, or from about 0.5 to about 2 meters.

The heat exchange channels 216 may be microchannels or they may have larger dimensions that would classify them as not being microchannels. Each of the heat exchange channels 216 may have a cross section having any shape, for example, a square, rectangle, circle, semi-circle, etc. The internal height of each heat exchange channel 216 may be considered to be the smaller of the internal dimensions normal to the direction of flow of heat exchange fluid in the heat exchange channels. Each of the heat exchange channels 216 may have an internal height of up to about 10 mm, or up to about 5 mm, or up to about 2 mm, or in the range of about 0.05 to about 10 mm, or from about 0.05 to about 5 mm, or from about 0.05 about 2 mm, or about 0.05 to about 1.5 mm. The width of each of these channels, which would be the other internal dimension normal to the direction of flow of heat exchange fluid through the heat exchange channel, may be of any dimension, for example, up to about 3 meters, or from about 0.1 to about 3 meters. The length of each of the heat exchange channels 216 may be of any dimension, for example, up to about 10 meters, or from about 0.1 to about 10 meters, or from about 0.2 to about 6 meters, or from 0.5 to about 3 meters, or from about 0.5 to about 2 meters.

The number of repeating units 210 or 210A in the microchannel reactor 110 may be an desired number, for example, one, two, three, four, six, eight, ten, hundreds, thousands, tens of thousands, hundreds of thousands, millions, etc.

In the design of a Fischer-Tropsch microchannel reactor it may be advantageous to provide a tailored heat exchange profile along the length of the process microchannels in order to optimize the reaction. This may be accomplished by matching the local release of heat given off by the Fischer-Tropsch reaction conducted in the process microchannels with heat removal or cooling provided by heat exchange fluid in heat exchange channels in the microchannel reactor. The extent of the Fischer-Tropsch reaction and the consequent heat release provided by the reaction may be higher in the front or upstream sections of the reaction zones in the process microchannels as compared to the back or downstream sections of the reaction zones. Consequently, the matching cooling requirements may be higher in the upstream section of the reaction zones as compared to the downstream sections of the reaction zones. Tailored heat exchange may be accomplished by providing more heat exchange or cooling channels, and consequently the flow of more heat exchange or cooling fluid, in thermal contact with upstream sections of the reaction zones in the process microchannels as compared to the downstream sections of the reaction zones. Alternatively or additionally, a tailored heat exchange profile may be provided by varying the flow rate of heat exchange fluid in the heat exchange channels. In areas where additional heat exchange or cooling is desired, the flow rate of the heat exchange fluid may be increased as compared to areas where less heat exchange or cooling is required. For example, a higher rate of flow of heat exchange fluid may be advantageous in the heat exchange channels in thermal contact with the upstream sections of the reaction zones in the process microchannels as compared to the heat exchange channels in thermal contact with the downstream sections of the reaction zones. Thus, in referring to FIG. 5, for example, a higher rate of flow in the heat exchange channels 216 near the inlet to the process microchannel 212 or reaction zone 220 may be used as compared to the heat exchange channels 216 near the outlet of the process microchannel 212 or reaction zone 220 where the flow rate may be less. Heat transfer from the process microchannels to the heat exchange channels may be designed for optimum performance by selecting optimum heat exchange channel dimensions and/or the rate of flow of heat exchange fluid per individual or groups of heat exchange channels. Additional design alternatives for tailoring heat exchange may relate to the selection and design of the Fischer-Tropsch catalyst (such as, particle size, catalyst formulation, packing density, use of a graded catalyst, or other chemical or physical characteristics) at specific locations within the process microchannels. These design alternatives may impact both heat release from the process microchannels as well as heat transfer to the heat exchange fluid. Temperature differentials between the process microchannels and the heat exchange channels, which may provide the driving force for heat transfer, may be constant or may vary along the length of the process microchannels.

The Fischer-Tropsch process microchannels and heat exchange channels may have rectangular cross sections and be aligned in side-by-side vertically oriented planes or horizontally oriented stacked planes. These planes may be tilted at an inclined angle from the horizontal. These configurations may be referred to as parallel plate configurations. These channels may be arranged in modularized compact units for scale-up. These may be in the form of cubic blocks as shown in FIGS. 3 and 4.

The microchannel reactor 110 may be made of any material that provides sufficient strength, dimensional stability and heat transfer characteristics to permit operation of the desired process. These materials may include aluminum; titanium; nickel; platinum; rhodium; copper; chromium; alloys of any of the foregoing metals; brass; steel (e.g., stainless steel); quartz; silicon; or a combination of two or more thereof. Each microchannel reactor may be constructed of stainless steel with one or more copper or aluminum waveforms being used for forming the channels.

The microchannel reactor 110 may be fabricated using known techniques including wire electrodischarge machining, conventional machining, laser cutting, photochemical machining, electrochemical machining, molding, water jet, stamping, etching (for example, chemical, photochemical or plasma etching) and combinations thereof.

The microchannel reactor 110 may be constructed by forming shims with portions removed that allow flow passage. A stack of shims may be assembled via diffusion bonding, laser welding, diffusion brazing, and similar methods to form an integrated device. The microchannel reactors may be assembled using a combination of shims or laminae and partial sheets or strips. In this method, the channels or void areas may be formed by assembling strips or partial sheets to reduce the amount of material required.

The microchannel reactor 110 may comprise a plurality of plates or shims in a stack defining a plurality of Fischer-Tropsch process layers and a plurality of heat exchange layers, each plate or shim having a peripheral edge, the peripheral edge of each plate or shim being welded to the peripheral edge of the next adjacent plate or shim to provide a perimeter seal for the stack. This is shown in U.S. application Ser. No. 13/275,727, filed Oct. 18, 2011, which is incorporated herein by reference.

The microchannel reactor 110 may be constructed using waveforms in the form of right angled corrugated inserts. These right angled corrugated sheets may have rounded edges rather than sharp edges. These inserts may be sandwiched between opposing planar sheets or shims. This is shown in FIG. 4. In this manner the microchannels may be defined on three sides by the corrugated insert and on the fourth side by one of the planar sheets. The process microchannels as well as the heat exchange channels may be formed in this manner. Microchannel reactors made using waveforms are disclosed in WO 2008/030467, which is incorporated herein by reference.

The process microchannels may contain one or more surface features in the form of depressions in and/or projections from one or more interior walls of the process microchannels. The surface features may be used to disrupt the flow of fluid flowing in the channels. These disruptions in flow may enhance mixing and/or heat transfer. The surface features may be in the form of patterned surfaces. The microchannel reactor may be made by laminating a plurality of shims together. One or both major surfaces of the shims may contain surface features. Alternatively, the microchannel reactor may be assembled using some sheets or shims and some strips, or partial sheets to reduce the total amount of metal required to construct the device. A shim containing surface features may be paired (on opposite sides of a microchannel) with another shim containing surface features. Pairing may create better mixing or heat transfer enhancement as compared to channels with surface features on only one major surface. The patterning may comprise diagonal recesses that are disposed over substantially the entire width of a microchannel surface. The patterned surface feature area of a wall may occupy part of or the entire length of a microchannel surface. Surface features may be positioned over at least about 10%, or at least about 20%, or at least about 50%, or at least about 80% of the length of a channel surface. Each diagonal recesses may comprise one or more angles relative to the flow direction. Successive recessed surface features may comprise similar or alternate angles relative to other recessed surface features.

The Fischer-Tropsch process microchannels may be characterized by having bulk flow paths. The term "bulk flow path" refers to an open path (contiguous bulk flow region) within the process microchannels or combustion channel. A contiguous bulk flow region allows rapid fluid flow through the channels without large pressure drops. In one embodiment, the flow of fluid in the bulk flow region is laminar. Bulk flow regions within each process microchannel or combustion channel may have a cross-sectional area of about 0.05 to about 10,000 mm$^2$, or about 0.05 to about 5000 mm$^2$, or about 0.1 to about 2500 mm$^2$. The bulk flow regions may comprise from about 5% to about 95%, or about 30% to about 80% of the cross-section of the process microchannels or combustion channel.

The contact time of the reactants with the Fischer-Tropsch catalyst may range up to about 2000 milliseconds (ms), or in the range from about 10 to about 2000 ms, or from about 10 ms to about 1000 ms, or about 20 ms to about 500 ms, or from about 200 to about 400 ms, or from about 240 to about 350 ms.

The space velocity (or gas hourly space velocity (GHSV)) for the flow of fluid in the Fischer-Tropsch microchannels may be at least about 1000 hr$^{-1}$ (normal liters of feed/hour/liter of volume within the process microchannels), or from about 1000 to about 1,000,000 hr$^{-1}$, or from about 5000 to about 20,000 hr$^{-1}$.

The pressure within the Fischer-Tropsch process microchannels may be up to about 100 atmospheres, or in the range from about 1 to about 100 atmospheres, or from about 1 to about 75 atmospheres, or from about 2 to about 40 atmospheres, or from about 2 to about 10 atmospheres, or from about 10 to about 50 atmospheres, or from about 20 to about 30 atmospheres.

The pressure drop of fluids as they flow in the Fischer-Tropsch process microchannels may range up to about 30 atmospheres per meter of length of channel (atm/m), or up to about 25 atm/m, or up to about 20 atm/m. The pressure drop may be in the range from about 10 to about 20 atm/m.

The Reynolds Number for the flow of fluid in the Fischer-Tropsch process microchannels may be in the range of about 10 to about 4000, or about 100 to about 2000.

The average temperature in the Fischer-Tropsch process microchannels may be in the range from about 150 to about 300° C., or in the range from about 175 to about 225° C., of in the range from about 190 to about 220° C., or from about 195 to about 215° C.

The heat exchange fluid entering the heat exchange channels of the microchannel reactor 110 may be at a temperature in the range of about 100° C. to about 400° C., or about 200° C. to about 300° C. The heat exchange fluid exiting the heat exchange channels may be at a temperature in the range of about 150° C. to about 450° C., or about 200° C. to about 350° C. The residence time of the heat exchange fluid in the heat exchange channels may range from about 1 to about 2000 ms, or about 10 to about 500 ms. The pressure drop for the heat exchange fluid as it flows through the heat exchange channels may range up to about 10 atm/m, or from about 1 to about 10 atm/m, or from about 3 to about 7 atm/m, or about 5 atm/m. The heat exchange fluid may be in the form of a vapor, a liquid, or a mixture of vapor and liquid. The Reynolds Number for the flow of the heat exchange fluid in heat exchange channels may be from about 10 to about 4000, or about 100 to about 2000.

The heat exchange fluid used in the heat exchange channels in the microchannel reactor 110 may be any heat exchange fluid suitable for cooling a Fischer-Tropsch exothermic reaction. These may include air, steam, liquid water, gaseous nitrogen, other gases including inert gases, carbon monoxide, oils such as mineral oil, and heat exchange fluids such as Dowtherm A and Therminol which are available from Dow-Union Carbide.

The heat exchange channels used in the microchannel reactor 110 may comprise process channels wherein an endothermic process is conducted. These heat exchange process channels may be microchannels. Examples of endothermic processes that may be conducted in the heat exchange channels include steam reforming and dehydrogenation reactions. Steam reforming of an alcohol that occurs at a temperature in the range from about 200° C. to about 300° C. is an example of an endothermic process that may be used. The incorporation of a simultaneous endothermic reaction to provide an improved cooling may enable a typical heat flux of roughly an order of magnitude above convective cooling.

The heat exchange fluid may undergo a partial or full phase change as it flows in the heat exchange channels of the microchannel reactor 110. This phase change may provide additional heat removal from the process microchannels beyond that provided by convective cooling. For a liquid heat exchange fluid being vaporized, the additional heat being transferred from the Fischer-Tropsch process microchannels may result from the latent heat of vaporization required by the heat exchange fluid. In one embodiment, about 50% by weight of the heat exchange fluid may be vaporized, or about 35% by weight may be vaporized, or about 20% by weight may be vaporized, or about 10% by weight, or about 5% by weight may be vaporized, or about 2 to about 3% by weight may be vaporized.

The heat flux for heat exchange in the microchannel reactor 110 may be in the range from about 0.01 to about 500 watts per square centimeter of surface area of the one or more heat transfer walls of the process microchannels (W/cm²) in the microchannel reactor, or in the range from about 0.1 to about 250 W/cm², or from about 1 to about 125 W/cm², or from about 1 to about 100 W/cm², or from about 1 to about 50 W/cm², or from about 1 to about 25 W/cm², or from about 1 to about 10 W/cm². The range may be from about 0.2 to about 5 W/cm², or about 0.5 to about 3 W/cm², or from about 1 to about 2 W/cm².

The control of heat exchange during the Fischer-Tropsch reaction process may be advantageous for controlling selectivity towards the desired product due to the fact that such added cooling may reduce or eliminate the formation of undesired by-products from undesired parallel reactions with higher activation energies.

The pressure within each individual heat exchange channel in the microchannel reactor 110 may be controlled using passive structures (e.g., obstructions), orifices and/or mechanisms upstream of the heat exchange channels or in the channels. By controlling the pressure within each heat exchange channel, the temperature within each heat exchange channel can be controlled. A higher inlet pressure for each heat exchange channel may be used where the passive structures, orifices and/or mechanisms let down the pressure to the desired pressure. By controlling the temperature within each heat exchange channel, the temperature in the Fischer-Tropsch process microchannels can be controlled. Thus, for example, each Fischer-Tropsch process microchannel may be operated at a desired temperature by employing a specific pressure in the heat exchange channel adjacent to or in thermal contact with the process microchannel. This provides the advantage of precisely controlled temperatures for each Fischer-Tropsch process microchannel. The use of precisely controlled temperatures for each Fischer-Tropsch process microchannel provides the advantage of a tailored temperature profile and an overall reduction in the energy requirements for the process.

In a scale up device, for certain applications, it may be required that the mass of the process fluid be distributed uniformly among the microchannels. Such an application may be when the process fluid is required to be heated or cooled down with adjacent heat exchange channels. The uniform mass flow distribution may be obtained by changing the cross-sectional area from one parallel microchannel to another microchannel. The uniformity of mass flow distribution may be defined by Quality Index Factor (Q-factor) as indicated below. A Q-factor of 0% means absolute uniform distribution.

$$Q = \frac{\dot{m}_{max} - \dot{m}_{min}}{\dot{m}_{max}} \times 100$$

A change in the cross-sectional area may result in a difference in shear stress on the wall. In one embodiment, the Q-factor for the microchannel reactor 110 may be less than about 50%, or less than about 20%, or less than about 5%, or less than about 1%.

The superficial velocity for fluid flowing in the Fischer-Tropsch process microchannels may be at least about 0.01 meters per second (m/s), or at least about 0.1 m/s, or in the range from about 0.01 to about 100 m/s, or in the range from about 0.01 to about 10 m/s, or in the range from about 0.1 to about 10 m/s, or in the range from about 1 to about 100 m/s, or in the range from about 1 to about 10 m/s.

The free stream velocity for fluid flowing in the Fischer-Tropsch process microchannels may be at least about 0.001 m/s, or at least about 0.01 m/s, or in the range from about 0.001 to about 200 m/s, or in the range from about 0.01 to about 100 m/s, or in the range from about 0.01 to about 200 m/s.

The conversion of CO from the fresh synthesis gas in the reactant mixture may be about 70% or higher, or about 75% or higher, or about 80% or higher, or about 90% or higher, or about 91% or higher, or about 92% or higher, or from about 88% to about 95%, or from about 90% to about 94%, or from about 91% to about 93%. The one-pass conversion of CO for the CO in the reactant mixture (i.e., fresh synthesis gas plus recycled tail gas) may be in the range from about 65% to about 90%, or from about 70% to about 85%.

The selectivity to methane in the Fischer-Tropsch (FT) product may be in the range from about 0.01 to about 10%, or about 1% to about 5%, or about 1% to about 10%, or about 3% to about 9%, or about 4% to about 8%.

The Fischer-Tropsch product formed in the microchannel reactor 110 may comprise a gaseous product fraction and a liquid product fraction. The gaseous product fraction may include hydrocarbons boiling below about 350° C. at atmospheric pressure (e.g., tail gases through middle distillates). The liquid product fraction (the condensate fraction) may include hydrocarbons boiling above about 350° C. (e.g., vacuum gas oil through heavy paraffins).

The Fischer-Tropsch product fraction boiling below about 350° C. may be separated into a tail gas fraction and a condensate fraction, e.g., normal paraffins of about 5 to about 20 carbon atoms and higher boiling hydrocarbons, using, for example, a high pressure and/or lower temperature vapor-liquid separator, or low pressure separators or a combination of separators. The fraction boiling above about 350° C. (the condensate fraction) may be separated into a wax fraction boiling in the range of about 350° C. to about 650° C. after removing one or more fractions boiling above about 650° C. The wax fraction may contain linear paraffins of about 20 to about 50 carbon atoms with relatively small amounts of higher boiling branched paraffins. The separation may be effected using fractional distillation.

The Fischer-Tropsch product formed in the microchannel reactor 110 may include methane, wax and other heavy high molecular weight products. The product may include olefins such as ethylene, normal and iso-paraffins, and combinations thereof. These may include hydrocarbons in the distillate fuel ranges, including the jet or diesel fuel ranges.

Branching may be advantageous in a number of end-uses, particularly when increased octane values and/or decreased pour points are desired. The degree of isomerization may be greater than about 1 mole of isoparaffin per mole of n-paraffin, or about 3 moles of isoparaffin per mole of n-paraffin. When used in a diesel fuel composition, the product may comprise a hydrocarbon mixture having a cetane number of at least about 60.

The Fischer-Tropsch product may be further processed to form a lubricating base oil or diesel fuel. For example, the product made in the microchannel reactor 110 may be hydrocracked and then subjected to distillation and/or catalytic isomerization to provide a lubricating base oil, diesel fuel, aviation fuel, and the like. The Fischer-Tropsch product may be hydroisomerized using the process disclosed in U.S. Pat. Nos. 6,103,099 or 6,180,575; hydrocracked and hydroisomerized using the process disclosed in U.S. Pat. Nos. 4,943,672 or 6,096,940; dewaxed using the process disclosed in U.S. Pat. No. 5,882,505; or hydroisomerized and dewaxed using the process disclosed in U.S. Pat. Nos. 6,013,171, 6,080,301 or 6,165,949. These patents are incorporated herein by reference for their disclosures of processes for treating Fischer-Tropsch synthesized hydrocarbons and the resulting products made from such processes.

The hydrocracking reaction may be conducted in a hydrocracking microchannel reactor and may involve a reaction between hydrogen and the Fischer-Tropsch product flowing from the microchannel reactor 210, or one or more hydrocarbons separated from the Fischer-Tropsch product (e.g., one or more liquid or wax Fischer-Tropsch hydrocarbons). The Fischer-Tropsch product may comprise one or more long chain hydrocarbons. In the hydrocracking process, a desired diesel fraction, for example, may be increased by cracking a $C_{23+}$ fraction to mid range carbon numbers of $C_{12}$ to $C_{22}$. A wax fraction produced from the Fischer-Tropsch microchannel reactor 110 may be fed to the hydrocracking microchannel reactor with excess hydrogen for a triple phase reaction. Under reaction conditions at elevated temperatures and pressures, a fraction of the liquid feed may convert to a gas phase, while the remaining liquid fraction may flow along the catalyst. In conventional hydrocracking systems, a liquid stream forms. The use of a microchannel reactor for the hydrocracking reaction enables unique advantages on a number of fronts. These may include kinetics, pressure drop, heat transfer, and mass transfer.

The Fischer-Tropsch hydrocarbon products that may be hydrocracked in the hydrocracking microchannel reactor may comprise any hydrocarbon that may be hydrocracked. These may include hydrocarbons that contain one or more C—C bonds capable of being broken in a hydrocracking process. The hydrocarbons that may be hydrocracked may include saturated aliphatic compounds (e.g., alkanes), unsaturated aliphatic compounds (e.g., alkenes, alkynes), hydrocarbyl (e.g., alkyl) substituted aromatic compounds, hydrocarbylene (e.g., alkylene) substituted aromatic compounds, and the like.

The feed composition for the hydrocracking microchannel reactor may include one or more diluent materials. Examples of such diluents may include non-reactive hydrocarbon diluents, and the like. The diluent concentration may be in the range from zero to about 99% by weight based on the weight of the Fischer-Tropsch product, or from zero to about 75% by weight, or from zero to about 50% by weight. The diluents may be used to reduce the viscosity of viscous liquid reactants. The viscosity of the feed composition in the hydrocracking microchannel reactor may be in the range from about 0.001 to about 1 centipoise, or from about 0.01 to about 1 centipoise, or from about 0.1 to about 1 centipoise.

The ratio of hydrogen to Fischer-Tropsch product in the feed composition entering the hydrocracking microchannel reactor may be in the range from about 10 to about 2000 standard cubic centimeters (sccm) of hydrogen per cubic centimeter (ccm) of Fischer-Tropsch product, or from about 100 to about 1800 sccm/ccm, or from about 350 to about 1200 sccm/ccm. The hydrogen feed may further comprise water, methane, carbon dioxide, carbon monoxide and/or nitrogen.

The $H_2$ in the hydrogen feed may be derived from another process such as a steam reforming process (product stream with $H_2/CO$ mole ratio of about 3), a partial oxidation process (product stream with $H_2/CO$ mole ration of about 2), an autothermal reforming process (product stream with $H_2/CO$ mole ratio of about 2.5), a $CO_2$ reforming process (product stream with $H_2/CO$ mole ratio of about 1), a coal gassification process (product stream with $H_2/CO$ mole ratio of about 1), and combinations thereof. With each of these feed streams the $H_2$ may be separated from the remaining ingredients using conventional techniques such as membranes or adsorption.

The hydrocracked Fischer-Tropsch product may comprise a middle distillate fraction boiling in the range of about 260-700° F. (127-371° C.). The term "middle distillate" is intended to include the diesel, jet fuel and kerosene boiling range fractions. The terms "kerosene" and "jet fuel" boiling range are intended to refer to a temperature range of 260-550° F. (127-288° C.) and "diesel" boiling range is intended to refer to hydrocarbon boiling points between about 260 to about 700° F. (127-371° C.). The hydrocracked Fischer-Tropsch product may comprise a gasoline or naphtha fraction. These may be considered to be the $C_5$ to 400° F. (204° C.) endpoint fractions.

The Catalyst:
  Catalyst Precursor

A catalyst precursor is a material that may be activated to form a catalyst. The terms "catalyst" and "catalyst precursor" may be used herein interchangeably and will be understood accordingly to their specific context.

The catalyst precursor comprises at least one catalyst metal, such as cobalt, which may be present in oxide form, as elemental metal, in the form of its carbide or as a mixture of any of these. In particular, the catalyst precursor may comprise from about 10 to about 60% cobalt (based on the weight of the metal as a percentage of the total weight of the catalyst precursor), or from about 35 to about 50% of cobalt, or from about 40 to about 44% of cobalt, or about 42% of cobalt. The cobalt may be present as CoO and/or $Co_3O_4$.

The catalyst precursor may comprise a noble metal on the support that may be one or more of Pd, Pt, Rh, Ru, Re, Ir, Au, Ag and Os. The noble metal may be one or more of Pd, Pt, Rh, Ru, Ir, Au, Ag and Os. The noble metal may be one or more of Pt, Ru and Re. The noble metal may be Ru. As an alternative, or in addition, the noble metal may be Pt. The catalyst precursor may comprise from about 0.01 to about 30% in total of noble metal(s) (based on the total weight of all noble metals present as a percentage of the total weight of the catalyst precursor), or from about 0.05 to about 20% in total of noble metal(s), or from about 0.1 to about 5% in total of noble metal(s), or about 0.2% in total of noble metal(s).

If desired, the catalyst precursor may include one or more other metal-based components as promoters or modifiers. These metal-based components may also be present in the catalyst precursor at least partially as carbides, oxides or elemental metals. A suitable metal for the one or more other metal-based components may be one or more of Zr, Ti, V, Cr, Mn, Ni, Cu, Zn, Nb, Mo, Tc, Cd, Hf, Ta, W, Re, Hg, Tl and the 4f-block lanthanides. Suitable 4f-block lanthanides may be La, Ce, Pr, Nd, Pm, Sm, Eu, Gd, Tb, Dy, Ho, Er, Tm, Yb and/or Lu. The metal for the one or more other metal-based components may be one or more of Zn, Cu, Mn, Mo and W. The metal for the one or more other metal-based components may be one or more of Re and Pt. The catalyst precursor may comprise from about 0.01 to about 10% in total of other metal(s) (based on the total weight of all the other metals as a percentage of the total weight of the catalyst precursor), or from about 0.1 to about 5% in total of other metals, or about 3% in total of other metals.

The catalyst precursor may contain up to 10% carbon (based on the weight of the carbon, in whatever form, in the catalyst as percentage of the total weight of the catalyst precursor), or from about 0.001 to about 5% of carbon, or about 0.01% to about 1% of carbon. Alternatively, the catalyst precursor may be characterized by the absence of carbon.

Optionally, the catalyst precursor may contain a nitrogen-containing organic compound such as urea, or an organic ligand such as ammonia or a carboxylic acid, such as citric acid or acetic acid, which may be in the form of a salt or an ester.

The precursor may be activated to produce the Fischer-Tropsch catalyst, for instance by heating the catalyst precursor in hydrogen and/or a hydrocarbon gas, or in a hydrogen gas diluted with another gas, such as nitrogen and/or methane, to convert at least some of the carbides or oxides to elemental metal. In the active catalyst, the cobalt may optionally be at least partially in the form of its carbide or oxide.

Reducing Agent

The use of a carboxylic acid as a reducing agent may minimize or reduce the fracturing and fragmentation of the catalyst precursor, thereby allowing more of the catalyst precursor to be incorporated into the activated catalyst to be used in the Fischer-Tropsch reaction, because fewer catalyst precursor particles are produced below a minimum particle size criteria for achieving an acceptable reactor pressure drop (e.g. <340 kPa (or 50 psi)). In some cases, the need for screening the catalyst precursor to remove particles below a threshold size limit (for example, about 125 microns) may be eliminated. Without wishing to be bound by theory, it is believed that is because the reaction between the carboxylic acid and the catalyst metal precursor(s) is less violent than with other reducing agents (e.g. urea), yet the reaction is still effective to provide a highly active, stable and selective catalyst.

The carboxylic acid may be chosen such that it minimizes the fracturing of the catalyst precursor whilst still ultimately producing an effective catalyst. A mixture of two or more carboxylic acids may be used. The carboxylic acid may be an alpha-hydroxy carboxylic acid, such as citric acid, glycolic acid, lactic acid or mandelic acid.

As used herein the term "reducing agent" may also include that the agent acts additionally as a complexing agent.

Catalyst Metal Precursor

The catalyst metal precursor may be a cobalt-containing precursor. Suitable cobalt-containing precursors may include cobalt benzoylacetonate, cobalt carbonate, cobalt cyanide, cobalt hydroxide, cobalt oxalate, cobalt oxide, cobalt nitrate, cobalt acetate, cobalt acetylyactonate and cobalt carbonyl. These cobalt precursors can be used individually or can be used in combination. These cobalt precursors may be in the form of hydrates or in anhydrous form. In some cases, where the cobalt precursor is not soluble in water, such as cobalt carbonate or cobalt hydroxide, a small amount of nitric acid or a carboxylic acid may be added to enable the precursor to fully dissolve in the solution or suspension. The solution or suspension may contain little or no water, in which case the drying step in the method of forming the catalyst precursor may be omitted.

The catalyst metal precursor may be cobalt nitrate. Cobalt nitrate may react with the reducing agent during calcination to produce $Co_3O_4$.

The solution or suspension may contain at least one primary catalyst metal precursor, such as one of the above cobalt-containing precursors or a mixture of cobalt-containing precursors, and at least one secondary catalyst metal precursor. Such secondary catalyst metal precursor(s) may be present to provide a promoter and/or modifier in the catalyst. Suitable secondary catalyst metals may include noble metals, such as Pd, Pt, Rh, Ru, Ir, Au, Ag and Os, transition metals, such as Zr, Ti, V, Cr, Mn, Fe, Co, Ni, Cu, Zn, Nb, Mo, Tc, Cd, Hf, Ta, W, Re, Hg and Ti and the 4f-block lanthanides, such as La, Ce, Pr, Nd, Pm, Sm, Eu, Gd, Tb, Dy, Ho, Er, Tm, Yb and/or Lu.

The secondary catalyst metal may be one or more of Pd, Pt, Ru, Ni, Co (if not the primary catalyst metal), Fe (if not the primary catalyst metal), Cu, Mn, Mo, Re and W.

Catalyst Support

The catalyst may be dispersed on a surface modified support to anchor the catalyst particles and provide mechanical strength. The support may comprise a refractory metal oxide, carbide, carbon, nitride, or mixture of two or more thereof. The support may comprise alumina, zirconia, silica, titania, or a mixture of two or more thereof. The surface of the support may be modified by treating it with silica, titania, zirconia, magnesia, chromia, alumina, or a mixture of two or more thereof. The material used for the support and the material used for modifying the support may be different. While not wishing to be bound by theory, it is believed that the surface treatment provided for herein helps keep the Co from sintering during operation of the inventive Fischer-Tropsch process.

The support may comprise silica and the surface of the silica may be coated with an oxide refractory solid oxide, in particular titania. The catalyst support may be in the form of a structured shape, pellets or a powder.

The support may comprise a titania modified silica support. Titania ($TiO_2$) may be used to increase the stability (e.g. by decreasing deactivation) of the silica-supported catalyst.

The deactivation rate of the catalyst may thus be such that it can be used in a Fischer-Tropsch synthesis for e.g. more than about 300 hours, or more than about 3,000 hours, or more than about 12,000 hours, or more than about 15,000 hours, all before a catalyst regeneration is required.

At elevated temperatures, the catalyst material may react with the surface Si—OH groups on a silica support to generate silicate species which are not Fischer-Tropsch active and may not be readily reducible. This may lead to a loss in active surface area of the catalyst and therefore a drop in FTS activity.

Without wishing to be bound by theory, it is believed that dispersion of titania onto a silica surface occurs via consumption of the surface Si—OH groups with the subsequent forming of bridging Ti—O—Si bonds. Thus, modification of a silica support with a layer of titania may remove the Si—OH groups and thereby prevent the formation of silicates.

$TiO_2$ may comprise at least 11 wt %, or greater than 11 wt %, of the total weight of the catalyst support. In particular, the catalyst support may comprise 11-30 wt %, 11-25 wt %, 11-20 wt %, or 12-18 wt %, or 15-17 wt %, or about 16 wt % $TiO_2$ on silica ($SiO_2$).

In one embodiment, the catalyst precursor may comprise from about 40 to about 44 wt % Co, from about 0.1 to about 0.3 wt % Re, and from about 0.01 to about 0.05 wt % Pt (each expressed as a percentage of the total weight of the catalyst precursor); and a $TiO_2$-modified silica catalyst support, comprising from about 11 to about 30 wt % $TiO_2$ (expressed as a percentage of the total weight of the catalyst support).

The catalyst precursor may comprise 42 wt % Co, 0.2 wt % Re, and 0.03 wt % Pt (each expressed as a percentage of the total weight of the catalyst precursor); and a $TiO_2$-modified silica catalyst support, comprising 16 wt % $TiO_2$ (expressed as a percentage of the total weight of the catalyst support).

The catalyst may be in the form of a particulate catalyst with a particle size distribution of d10 greater than 90 μm and d90 less than 325 μm. The mean particle size distribution may be between about 180 and about 300 μm.

As titania is more acidic than silica, the efficacy of the dispersion of titania onto the silica surface may be characterized by measurement of the surface acidity of the modified support. In addition, the presence of tetrahedrally coordinated $Ti^{4+}$ ions at the silica/titania interface may generate further, particularly strong, Lewis acid sites.

The surface acidity of the modified support may be measured using Temperature Programmed Desorption (TPD) experiments with a Lewis base such as ammonia.

In one embodiment, the surface acidity of the catalyst support may be such that neutralization requires 0.20 μmol $NH_3/m^2$ or more, e.g. 0.22 μmol $NH_3/m^2$ or more.

Another method for measurement of the replacement of Si—OH bonds with Ti—O—Si on a modified support is through the use of FT-IR spectroscopy. In FT-IR, a band for a Si—OH groups is expected at a frequency of approximately 980 $cm^{-1}$. In addition, a band for a Ti—O—Si groups is expected at a frequency of approximately 950 $cm^{-1}$. Therefore, as the number of Si—OH bonds are replaced by Ti—O—Si groups, the intensity of the band at 980 $cm^{-1}$ is reduced and the intensity of the band at 950 $cm^{-1}$ is increased. The ratio of the intensities of the bands at 980 $cm^{-1}$ and 950 $cm^{-1}$ provides an indication of how many Si—OH groups have been replaced with Ti—O—Si groups.

The FT-IR spectra may be corrected by subtracting a spectrum for silica. Therefore, the band at 980 $cm^{-1}$ may appear, in these corrected spectra, as a dip. The "FT-IT intensity ratio" may be calculated using the observed intensities of the 980 $cm^{-1}$ and 950 $cm^{-1}$ bands in the corrected spectra, with the intensity of the band maximum at 950 $cm^{-1}$ being divided by the intensity of the band minimum at 980 $cm^{-1}$.

The modified catalyst support may have a ratio of FT-IR intensities at 950:980 $cm^{-1}$ of 1.2 or more, e.g. 1.3 or more, 1.4 or more or 1.5 or more.

Deactivation Rate

The catalyst may be used for an extended period (e.g. >300 hours) with a deactivation rate of less than about 1.4% per day, or less than about 1.2% per day, or between about 0.1% and about 1.0% per day, or between about 0.03 and about 0.15% per day.

The catalyst may have a deactivation rate in a fixed-bed combinatorial reactor or high throughput screening reactor measured as percent loss of CO conversion per 24 hours wherein the CO conversion may b greater than about 70%, or greater than about 75%, or greater than about 80%, wherein the loss is measured over a period of 200 hours or more, and wherein the period of 200 hours starts at a time on stream (TOS) of less than 500 hours.

The catalyst may be used for an extended period (e.g. >300 hours) with a deactivation rate of less than about 0.25% per day, or between about 0.001% and about 0.20% per day, or between about 0.01 and about 0.10% per day, or about 0.08% per day in a microchannel reactor.

The catalyst may have a deactivation rate in a microchannel reactor measured as percent loss of CO conversion per 24 hours of less than about 0.25, wherein the CO conversion is greater than about 70%, or greater than about 75%, or greater than about 80%, wherein the loss is measured over a period of 200 hours or more, and wherein the period of 200 hours starts at a time on stream (TOS) of less than 500 hours.

$Co_3O_4$ Average Particle Diameter and Size Distribution

The activity and the selectivity of cobalt-based catalysts may be influenced by the density of active sites, favouring very small particle sizes. However, the deactivation mechanisms of cobalt catalysts may follow in general the reverse trend, where the largest particles may be the most stable.

The numerical average particle diameter of $Co_3O_4$ may be less than about 12 nm (determined by powder X-ray diffraction, for example, using a Siemens D5000 theta/theta powder diffractometer and $CuK_\alpha$ radiation). The cobalt oxide particle size distribution may influence catalyst activity and stability, such that, a particle size distribution as narrow as possible may be useful. The width of the particle size distribution can be measured by the c value of the lognormal particle size distribution. c is a dimensionless ratio, and characterizes the width of the size distribution. The c value of the lognormal particle size distribution of $Co_3O_4$ particles may be less than about 0.31. The average particle diameter of $Co_3O_4$ may be below about 11 nm, or between about 8 and about 10 nm. The c value may be between about 0.19 and about 0.31, or below about 0.25, or between about 0.19 and about 0.25. Where the numerical average particle diameter of the $Co_3O_4$ is in the range of about 8 to about 10 nm, c may be less than 0.31.

The numerical average particle diameter may be in the range from about 8 to about 10 nm, the c-value may be about 0.31 or less, e.g. 0.29 or less, 0.26 or less or 0.25 or less.

Alternatively or in addition, the c-value may be about 0.19 or more, e.g. 0.20 or more or 0.235 or more. The c-value may be about 0.19≤c≤0.31; 0.19≤c≤0.29; 0.19≤c≤0.26; 0.19≤c≤0.25; 0.20≤c≤0.31; 0.20≤c≤0.29; 0.20≤c≤0.26; 0.20≤c≤0.25; 0.235≤c≤0.31; 0.235≤c≤0.29; 0.235≤c≤0.26; or 0.235≤c≤0.25.

In a sample of calcined catalyst (assuming spherical particles equivalent to crystallites or crystallites with a lognormal monomodal distribution) the form of the particle size distribution may be written as:

$$f(R) = \frac{1}{R\sqrt{2\pi \ln(1+c)}} e^{-\frac{[\ln(\frac{R}{R_O}\sqrt{1+c})]^2}{2\ln(1+c)}} \quad \text{where}$$

$$c = \frac{\sigma^2}{R_O^2}$$

Equation 1 where $R_O$ is the numeric average particle radius and c, which is known as the dimensionless ratio, characterizes the width of the size distribution. Multiplication of $R_O$ by 2 yields the numerical average particle diameter.

An alternative way to characterize the relationship between the $Co_3O_4$ particle size distribution and the catalyst's activity and stability is through the D-value. The D-value may be referred to as a reformulation of the size distribution as described by the c-value and does not represent any new data. Therefore, the c- and D-values are mathematically related, but an improved correlation may be seen between the D-value and the catalyst's activity and stability.

The D-value is calculated from parameters of the particle size distribution of $Co_3O_4$ particles in a fresh, unreduced catalyst, i.e. in a catalyst precursor Trends between the c-value and the deactivation rate can be seen for $Co_3O_4$ particles of substantially the same numerical average particle diameter. The D-value may be an improvement on the c-value because, while it still takes into account both the width of the $Co_3O_4$ particle size distribution and the numerical average particle diameter, it places a larger weighting on the numerical average $Co_3O_4$ particle diameter, which removes the need to maintain substantially the same numerical average particle diameter in order to observe trends in the data. This enables a single metric (D-value) to be reported and compared, rather than two metrics (c-value and numerical average particle diameter).

The D-value may be calculated by plotting the lognormal particle size distribution using Equation 1 (see above). The frequency at the mode of this lognormal distribution ($f_{mode}$) may be considered to be a measure of the width of the distribution. In order to account for the dependence of the FTS catalyst stability on numerical average particle diameter, the below formula in which $f_{mode}$ is weighted by the size distribution median to create a "size-weighted distributed breadth", or D-value, may be used:

$$D = f_{mode}{}^y \times R_O \times 2$$

Equation 2 wherein $f_{mode}$ is the frequency at the mode of the lognormal distribution, $R_O$ is the numeric average particle radius, and y is an empirical value based on experimental observation. The value of y is determined via comparison of the stability of a selection of catalysts (at least about 5 to 10) with substantially similar compositions but small variations in $Co_3O_4$ particle size and size distribution width. These variations may be achieved via minor modifications of the synthesis method e.g. increasing the dilution of the impregnation solution (which is shown in an example to cause subtle changes to the particle size distribution). FTS stability data on these catalysts under the same testing conditions is then collected. Within this set of similar catalysts, y is then manually adjusted to create a spread of D-values such that catalysts which are FTS stable can be distinguished from catalysts which are not stable. For the catalyst composition 42% Co-0.2% Re-0.03% Pt on 16% $TiO_2/SiO_2$, the y value is 1.15.

Therefore, an increase in the D-value may represent either a narrowing of the particle size distribution or an increase in the numerical average particle diameter.

The $Co_3O_4$ particle size distribution may influence catalyst FTS activity and stability, such that, preferably, the D-value of the lognormal particle size distribution of $Co_3O_4$ particles is about 19 or more. A D-value of 19.2 corresponds to a size distribution with a c-value of about 0.31 and numerical average particle diameter of about 10 nm. A D-value of 19.8 corresponds to a size distribution with a c-value of about 0.31 and an average particle size of about 8 nm. In either of these cases, a decrease in c (e.g. narrowing of the size distribution) would result in an increase in D. Therefore the specification of c≤0.31 over the average particle size range 8-10 nm corresponds to particle distributions defined by having D-values greater than or equal to about 19.

In one embodiment, the D-value may be about 19 or more, e.g. 19.2 or more, 20.4 or more, 21.0 or more or 21.35 or more, or 21.4 or more. Alternatively or in addition, the D-value may be 23.5 or less, e.g. 22.2 or less. It is within the scope of the present application to combine any of these upper and lower limits such that the D-value may be about 19≤D≤23.5; 19≤D≤22.2; 19.2≤D≤23.5; 19.2≤D≤22.2; 20.4≤D≤23.5; 20.4≤Dc≤22.2; 21.0≤D≤23.5; 21.0≤Dc≤22.2; 21.35≤D≤23.5; or 21.35≤D≤22.2.

The catalyst or catalyst precursor may comprise a 16% $TiO_2$ modified silica support comprising $Co_3O_4$ on the support having an average particle size of about 9.6 nm, a c-value of about 0.31 and a D-value of about 19.2. Alternatively, the catalyst or catalyst precursor may comprise a 16% $TiO_2$ modified silica support comprising $Co_3O_4$ on the support having an average particle size of about 6.2 nm, a c-value of about 0.14 and a D-value of about 29.1.

The characteristics of the $Co_3O_4$ particles may be affected by the synthetic procedure by which the catalyst precursor and catalyst are produced.

In particular, where the catalyst comprises a $TiO_2$-modified silica support, the use of a titanium alkoxide (e.g. titanium isopropoxide) to modify the support can provide a catalyst comprising $Co_3O_4$ having the above properties. In this embodiment, the catalyst precursor may contain less than 10%, or less than 5%, or preferably less than 1% crystalline $TiO_2$ (expressed as a percentage of all of the $TiO_2$ in the catalyst precursor). Alternatively, all of the $TiO_2$ present in the catalyst precursor may be amorphous or not crystalline (up to detectable limits).

Alternatively, where the catalyst comprises a $TiO_2$-modified silica support, an aqueous method (e.g. using titanium (IV) bis(ammoniumlactato)dihydroxide) may be used to modify the support in place of using a titanium alkoxide. A preferred aqueous method is as described in the section headed "Aqueous Treating of Catalyst Support" below. The resulting modified support is also able to provide a catalyst comprising $Co_3O_4$ having the above properties.

Similarly, the use of citric acid as fuel/reducing agent in the production of the catalyst precursor can provide a catalyst precursor and a catalyst comprising $Co_3O_4$ having the above properties.

Also, the number of impregnations used to form a catalyst may affect the particle size distribution and therefore the c value. Specifically, an increase in the number of impregnations may result in an increase in the c value and an increase in the deactivation rate of the catalyst. Therefore, a reduced number of impregnation steps is preferred. Three impregnation steps may be used.

In one embodiment, the catalyst may be formed using 4 impregnations resulting in a c value of 0.25, preferably with the numerical average particle diameter of $Co_3O_4$ in the range from about 8 to about 10 nm.

In one embodiment, the catalyst may be formed using 6 impregnations resulting in a c value of 0.27, preferably with the numerical average particle diameter of $Co_3O_4$ in the range from about 8 to about 10 nm.

In one embodiment, the catalyst may be formed using 8 impregnations resulting in a c value of 0.30, preferably with the numerical average particle diameter of $Co_3O_4$ in the range from about 8 to about 10 nm.

Catalyst Precursor Preparation

Catalyst precursors may be prepared by the method defined above or by any of the methods discussed in WO 2008/104793. The solution or suspension may be applied to the catalyst support by spraying, impregnating or dipping. If the solution or suspension contains no water at all there is no need for the drying step and the calcination step can be carried out directly after the deposition step.

However, if a catalyst metal precursor which is a hydrate is used, the solution or suspension may contain some water of hydration. This water may be sufficient to dissolve some of the components of the solution or suspension, such as the carboxylic acid (if solid at room temperature). However, in some cases, it may be necessary to add some water to the solution or suspension in order to ensure that the catalyst metal precursor(s) and the other components are able to dissolve or become suspended. In such cases, the amount of water used is usually the minimum required to allow the catalyst metal precursor(s) and the other components to dissolve or be suspended.

The deposition, drying and calcination steps may be repeated one or more times. For each repeat, the solution or suspension used in the deposition step may be the same or different. If the solution or suspension in each repetition is the same, the repetition of the steps allows the amount of catalyst metal(s) to be brought up to the desired level on the catalyst support stepwise in each repetition. If the solution or suspension in each repetition is different, the repetition of the steps allows schemes for bringing the amounts of different catalyst metals up to the desired level in a series of steps to be executed.

A programmed heating regime may be used during drying and calcination which increases the temperature gradually so as to control gas and heat generation from the catalyst metal precursors and the other components of the solution or suspension.

During the heating processes, the catalyst support may reach a maximum temperature of no more than about 500° C., or no more than about 375° C., or no more than about 250° C. at atmospheric pressure.

The temperature may be ramped up at a rate of from about 0.0001 to about 10° C. per minute, or from about 0.1 to about 5° C. per minute. The rates may be in the range from about 10 to about 30° C. per minute.

An illustrative programmed heating regime may comprise:
(a) heating the catalyst support onto which the solution or suspension has been deposited at a rate of about 1 to about 5° C. per minute, or about 2° C. per minute to a temperature of about 80 to about 120° C., or about 100° C. and maintaining it at this temperature for about 1 to about 10 hours, or about 5 hours;
(b) heating it at a rate of about 1 to about 5° C. per minute, or about 2° C. per minute to a temperature of about 150 to about 400° C., or about 200 to about 350° C., or about 250° C. and maintaining it at this temperature for about 0.5 to about 6 hours, or about 1 to about 6 hours, or about 3 hours.

The heating steps can be carried out in a rotating kiln, in a static oven or in a fluidised bed.

Once the calcination step has been completed, either after the steps are first carried out or at the end of a repetition, further catalyst metals may optionally be loaded onto the catalyst support.

The calcination step may be carried out in an oxygen-containing atmosphere (e.g. air), in particular if metal catalyst oxides are to be formed.

Catalyst Activation

The catalyst precursor may be activated by any of the conventional activation processes. For instance, the catalyst precursor may be activated using a reducing gas, such as hydrogen, a gaseous hydrocarbon, a mixture of hydrogen and a gaseous hydrocarbon (e.g. methane), a mixture of gaseous hydrocarbons, a mixture of hydrogen and gaseous hydrocarbons, a mixture of hydrogen and nitrogen, syngas, or a mixture of syngas and hydrogen.

The gas may be at a pressure of from 1 bar (atmospheric pressure) to about 100 bar, or at a pressure of less than about 30 bar. The pressure may be in the range from about 5 to about 20 bar, or from about 10 to about 15 bar.

The catalyst precursor may be heated to its activation temperature at a rate of from about 0.01 to about 20° C. per minute. The activation temperature may be no more than about 600° C., or no more than about 400° C. The activation temperature may be in the range from about 300° C. to about 400° C., or from about 325° C. to about 375° C., or about 350° C.

The catalyst precursor may be held at the activation temperature for about 2 to about 24 hours, or about 8 to about 12 hours.

After activation, the catalyst may be cooled to a desired reaction temperature.

The catalyst, after activation, may be used in the above-described Fischer-Tropsch process.

In a Fischer Tropsch reaction carried out in a microchannel reactor comprising using the disclosed catalyst or a catalyst derived from the disclosed catalyst precursor, the performance of the catalyst may be substantially maintained over a reaction period of about 5000 hours or more without regeneration of the catalyst, such that the contact time may be less than 500 milliseconds, the CO conversion may be greater than about 70% and the methane selectivity may be less than about 10%.

By "performance of the catalyst is substantially maintained" is meant that the average contact time, the average CO conversion and the average methane selectivity parameters during each data collection interval of 24 hours may be in the ranges described above. The data collection interval may be 12 hours, 6 hours, 3 hours or 1 hour in duration. In this way, although there may be minor variations of these parameters, the overall performance of the catalyst in terms of the contact time, CO conversion and methane selectivity may be maintained.

The reaction period may be about 8000 hours or more. In a Fischer Tropsch reaction comprising using the disclosed catalyst or a catalyst derived from the disclosed catalyst precursor, the deactivation rate of the catalyst measured as percent loss of CO conversion per day may be about 0.09% or less over a reaction period of about 5000 hours or more.

The catalyst may have any size and geometric configuration that fits within the process microchannels. The catalyst may be in the form of particulate solids (e.g., pellets, powder, fibers, and the like) having a median particle diameter of about 1 to about 1000 µm (microns), or about 10 to about 500 µm, or about 25 to about 250 µm. The median particle diameter may be in the range from about 125 to about 400 µm, or about 170 to about 300 µm. In one embodiment, the catalyst may be in the form of a fixed bed of particulate solids.

Figure 7:
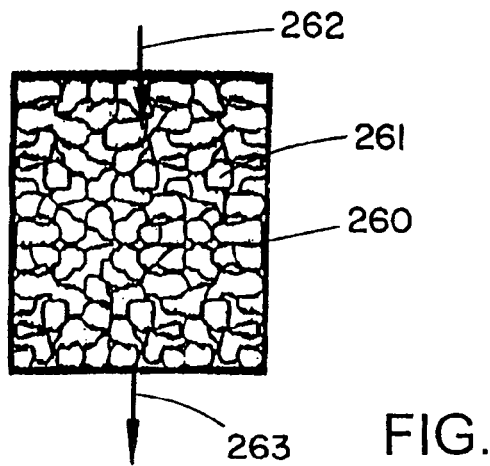
FIGS. 7-12 are schematic illustrations of catalysts or catalyst supports that may be used in the process microchannels. The catalyst illustrated in FIG. 7 is in the form of a bed of particulate solids. The catalyst illustrated in FIG. 8 has a flow-by design. The catalyst illustrated in FIG. 9 has a flow-through structure.

The catalyst may be in the form of a fixed bed of particulate solids (as shown in FIG. 7). Referring to FIG. 7, the catalyst 261, which is in the form of a bed of particulate solids, is contained in process microchannel 260. Reactants enter the fixed bed as indicated by arrow 262, undergo reaction, and product flows out of the fixed bed as indicated by arrow 263.

The catalyst may be supported on a catalyst support structure such as a foam, felt, wad or a combination thereof. The catalyst support structure may comprise a fin assembly or corrugated inserts suitable for insertion into slots in the microchannel reactor. The cobalt loading for the catalyst may be at least about 20% by weight, or at least about 25% by weight, or at least about 28% by weight, or at least about 30% by weight, or at least about 32% by weight, or at least about 35% by weight, or at least about 38% by weight.

The term "foam" is used herein to refer to a structure with continuous walls defining pores throughout the structure. The term "felt" is used herein to refer to a structure of fibers with interstitial spaces therebetween. The term "wad" is used herein to refer to a structure of tangled strands, like steel wool. The catalyst may be supported on a honeycomb structure. The catalyst may be supported on a flow-by support structure such as a felt with an adjacent gap, a foam with an adjacent gap, a fin structure with gaps, a washcoat on any inserted substrate, or a gauze that is parallel to the flow direction with a corresponding gap for flow.

Figure 8:
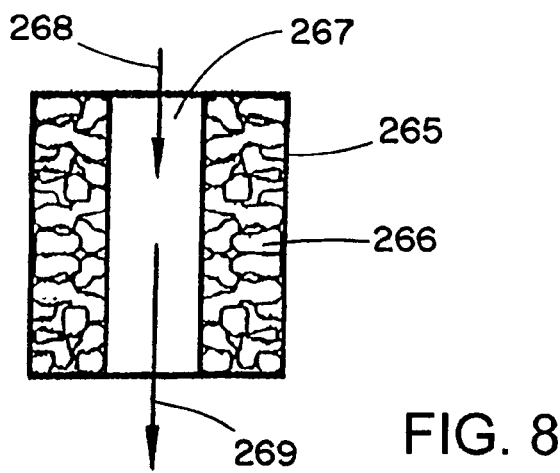

An example of a flow-by structure is illustrated in FIG. 8. In FIG. 8, the catalyst 266 is contained within process microchannel 265. An open passage way 267 permits the flow of fluid through the process microchannel 265 as indicated by arrows 268 and 269. The reactants contact the catalyst and undergo reaction to form product.

Figure 9:
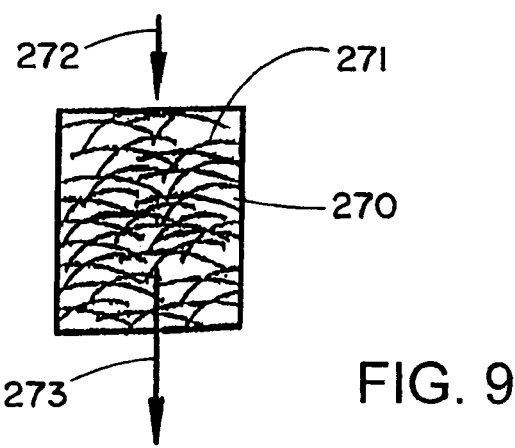

The catalyst may be supported on a flow-through support structure such as a foam, wad, pellet, powder, or gauze. An example of a flow-through structure is illustrated in FIG. 9. In FIG. 9, the flow-through catalyst 271 is contained within process microchannel 270, the reactants flow through the catalyst 271 as indicated by arrows 272 and 273, and undergo reaction to form the product.

The support structure for a flow-through catalyst may be formed from a material comprising silica gel, foamed copper, sintered stainless steel fiber, steel wool, alumina, or a combination of two or more thereof. The support structure may be made of a heat conducting material, such as a metal, to enhance the transfer of heat to or from the catalyst.

Figure 10:
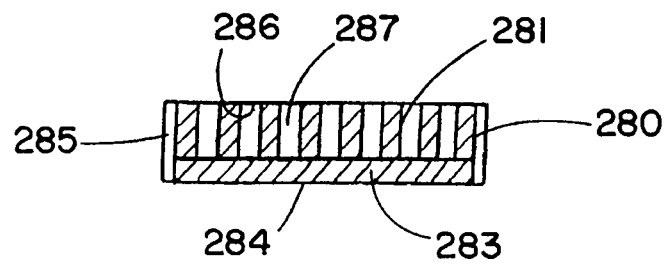
Figure 11:
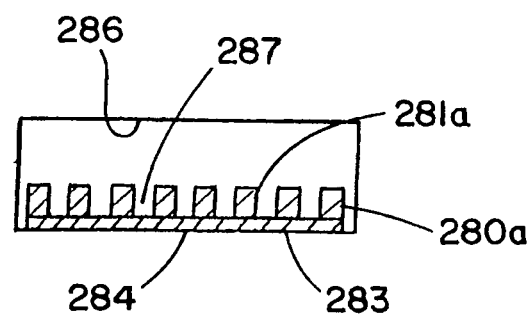
Figure 12:
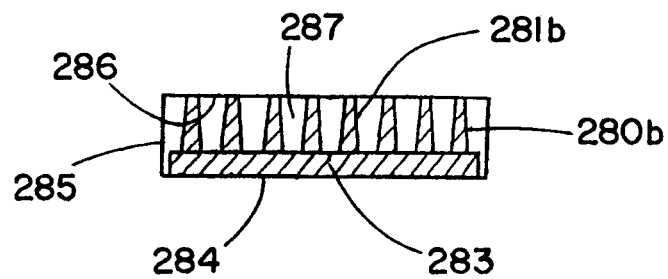

The catalyst may be supported on a fin assembly comprising one or more fins positioned within the process microchannels. Examples are illustrated in FIGS. 10-12. Referring to FIG. 10, fin assembly 280 includes fins 281 which are mounted on fin support 283 which overlies base wall 284 of process microchannel 285. The fins 281 project from the fin support 283 into the interior of the process microchannel 285. The fins 281 may extend to and contact the interior surface of upper wall 286 of process microchannel 285. Fin channels 287 between the fins 281 provide passage ways for reactant and product to flow through the process microchannel 285 parallel to its length. Each of the fins 281 has an exterior surface on each of its sides. The exterior surface provides a support base for the catalyst. The reactants may flow through the fin channels 287, contact the catalyst supported on the exterior surface of the fins 281, and react to form product. The fin assembly 280a illustrated in FIG. 11 is similar to the fin assembly 280 illustrated in FIG. 10 except that the fins 281a do not extend all the way to the interior surface of the upper wall 286 of the microchannel 285. The fin assembly 280b illustrated in FIG. 12 is similar to the fin assembly 280 illustrated in FIG. 10 except that the fins 281b in the fin assembly 280b have cross sectional shapes in the form of trapezoids. Each of the fins may have a height ranging from about 0.02 mm up to the height of the process microchannel 285, or from about 0.02 to about 10 mm, or from about 0.02 to about 5 mm, or from about 0.02 to about 2 mm. The width of each fin may range from about 0.02 to about 5 mm, or from about 0.02 to about 2 mm, or about 0.02 to about 1 mm. The length of each fin may be of any length up to the length of the process microchannel 285, or up to about 10 m, or about 0.5 to about 10 m, or about 0.5 to about 6 m, or about 0.5 to about 3 m. The gap between each of the fins may be of any value and may range from about 0.02 to about 5 mm, or from about 0.02 to about 2 mm, or from about 0.02 to about 1 mm. The number of fins in the process microchannel 285 may range from about 1 to about 50 fins per centimeter of width of the process microchannel 285, or from about 1 to about 30 fins per centimeter, or from about 1 to about 10 fins per centimeter, or from about 1 to about 5 fins per centimeter, or from about 1 to about 3 fins per centimeter. Each of the fins may have a cross-section in the form of a rectangle or square as illustrated in FIG. 10 or 11, or a trapezoid as illustrated in FIG. 12. When viewed along its length, each fin may be straight, tapered or have a serpentine configuration. The fin assembly may be made of any material that provides sufficient strength, dimensional stability and heat transfer characteristics to permit operation for which the process microchannel is intended. These materials include: steel (e.g., stainless steel, carbon steel, and the like); aluminum; titanium; nickel; platinum; rhodium; copper; chromium; alloys of any of the foregoing metals; monel; inconel; brass; polymers (e.g., thermoset resins); ceramics; glass; quartz; silicon; or a combination of two or more thereof. The fin assembly may be made of an $Al_2O_3$ or a $Cr_2O_3$ forming material wherein a layer of $Al_2O_3$ or a $Cr_2O_3$ forms on the surface of the fin assembly when the fin assembly is heat treated in air. The fin assembly may be made of an alloy comprising Fe, Cr, Al and Y, or an alloy comprising Ni, Cr and Fe.

Figure 14:
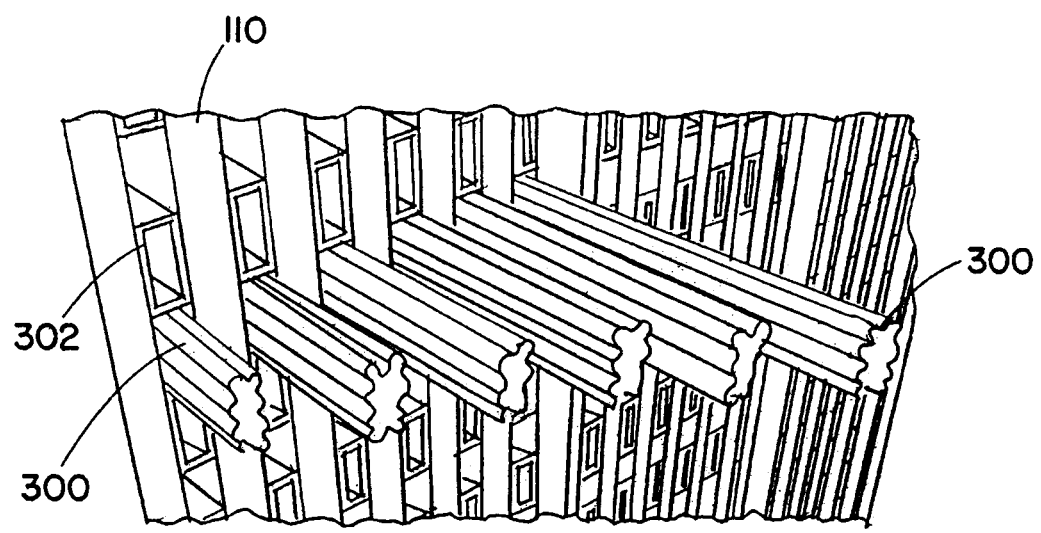
FIG. 14 is an illustration of catalyst inserts that may be used in the microchannel reactor.

The catalyst may be supported on one or more corrugated inserts positioned in slots within the microchannel reactor. This is illustrated in FIG. 14 wherein microchannel reactor 110 includes corrugated inserts 300 inserted in slots 302. The slots 302 may comprise microchannels, and have the dimensions indicated above as being microchannels. Alternatively, the slots 302 may have dimensions that would make them larger than microchannels. The process microchannels of the microchannel reactor may comprise the slots 302, or may be positioned within the corrugated inserts 300 and/or formed by openings between the interior sidewalls of the slots 302 and the inserts 300. Each of the corrugated inserts 300 may have a height ranging from about 0.02 mm up to the height of the slot 302, or from about 0.02 to about 10 mm, or from about 0.02 to about 5 mm, or from about 0.02 to about 2 mm. Each of the corrugated inserts 300 may have a width ranging from about 0.02 mm up to the width of the slot 302, or from about 0.02 to about 10 mm, or from about 0.02 to about 5 mm, or from about 0.02 to about 2 mm. The length of each corrugated insert may be of any length up to the length of the slot 302, or up to about 10 m, or about 0.5 to about 10 m, or about 0.5 to about 6 m, or about 0.5 to about 3 m. The corrugated inserts 300 may be made of any material that provides sufficient strength, dimensional stability and heat transfer characteristics to permit operation for which the microchannel reactor is intended. These materials include: steel (e.g., stainless steel, carbon steel, and the like); aluminum; titanium; nickel; platinum; rhodium; copper; chromium; alloys of any of the foregoing metals; monel; inconel; brass; polymers (e.g., thermoset resins); ceramics; glass; quartz; silicon; or a combination of two or more thereof. The corrugated inserts 300 may be made of an alloy that forms a layer of $Al_2O_3$ or $Cr_2O_3$ on the surface of the inserts when heat treated in air. The corrugated inserts 300 may be made of an alloy comprising Fe, Cr, Al and Y, or an alloy comprising Ni, Cr and Fe.

The catalyst may be directly washcoated or grown from solution on the interior walls of the process microchannels and/or on one or more of the above-described catalyst support structures. The catalyst may be in the form of a single piece of porous contiguous material, or many pieces in physical contact. The catalyst may comprise a contiguous material and have a contiguous porosity such that molecules can diffuse through the catalyst. In this embodiment, the fluids may flow through the catalyst rather than around it. The cross-sectional area of the catalyst may occupy from about 1 to about 99%, or about 10 to about 95% of the cross-sectional area of the process microchannels.

The catalyst may comprise a support, an interfacial layer on the support, and a catalyst material on or mixed with the interfacial layer. The support may comprise one or more of the above-described foams, felts, wads, fin structures, or corrugated inserts. The interfacial layer may be solution deposited on the support or it may be deposited by chemical vapor deposition or physical vapor deposition. The catalyst may comprise the support, a buffer layer, an interfacial layer, and the catalyst material. The support may be porous. Any of the foregoing layers may be continuous or discontinuous as in the form of spots or dots, or in the form of a layer with gaps or holes. The support may have a porosity of at least about 5% as measured by mercury porosimetry and an average pore size (sum of pore diameters divided by number of pores) of about 1 to about 2000 microns, or from about 1 to about 1000 microns. The support may be a porous ceramic or a metal foam. Other supports that may be used may include carbides, nitrides, and composite materials. The support may have a porosity of about 30% to about 99%, or about 60% to about 98%. The support may be in the form of a foam, felt, wad, or a combination thereof. The open cells of the metal foam may range from about 20 pores per inch (ppi) to about 3000 ppi, and in one embodiment about 20 to about 1000 ppi, and in one embodiment about 40 to about 120 ppi. The term "ppi" refers to the largest number of pores per inch (in isotropic materials the direction of the measurement is irrelevant; however, in anisotropic materials, the measurement is done in the direction that maximizes pore number).

The buffer layer, when present, may have a different composition and/or density than both the support and the interfacial layers, and in one embodiment has a coefficient of thermal expansion that is intermediate the thermal expansion coefficients of the porous support and the interfacial layer. The buffer layer may be a metal oxide or metal carbide. The buffer layer may comprise $Al_2O_3$, $TiO_2$, $SiO_2$, $ZrO_2$, or combination thereof. The $Al_2O_3$ may be $\alpha$-$Al_2O_3$, $\gamma$-$Al_2O_3$ or a combination thereof. The buffer layer may comprise an oxide layer (e.g. $Al_2O_3$ or $Cr_2O_3$) formed by heat treating the support in air. The buffer layer may be formed of two or more compositionally different sublayers. For example, when the porous support is metal, for example a stainless steel foam, a buffer layer formed of two compositionally different sublayers may be used. The first sublayer (in contact with the porous support) may be $TiO_2$. The second sublayer may be $\alpha$-$Al_2O_3$ which is placed upon the $TiO_2$. In one embodiment, the $\alpha$-$Al_2O_3$ sublayer is a dense layer that provides protection of the underlying metal surface. A less dense, high surface area interfacial layer such as alumina may then be deposited as support for a catalytically active layer.

The support may have a thermal coefficient of expansion different from that of the interfacial layer. In such a case a buffer layer may be needed to transition between the two coefficients of thermal expansion. The thermal expansion coefficient of the buffer layer can be tailored by controlling its composition to obtain an expansion coefficient that is compatible with the expansion coefficients of the porous support and interfacial layers. The buffer layer should be free of openings and pin holes to provide superior protection of the underlying support. The buffer layer may be nonporous. The buffer layer may have a thickness that is less than one half of the average pore size of the porous support. The buffer layer may have a thickness of about 0.05 to about 10 μm, or about 0.05 to about 5 μm.

In one embodiment adequate adhesion and chemical stability may be obtained without a buffer layer. In this embodiment the buffer layer may be omitted.

The interfacial layer may comprise nitrides, carbides, sulfides, halides, metal oxides, carbon, or a combination thereof. The interfacial layer provides high surface area and/or provides a desirable catalyst-support interaction for supported catalysts. The interfacial layer may be comprised of any material that is conventionally used as a catalyst support. The interfacial layer may comprise a metal oxide. Examples of metal oxides that may be used include $\alpha$-$Al_2O_3$, $SiO_2$, $ZrO_2$, $TiO_2$, tungsten oxide, magnesium oxide, vanadium oxide, chromium oxide, manganese oxide, iron oxide, nickel oxide, cobalt oxide, copper oxide, zinc oxide, molybdenum oxide, tin oxide, calcium oxide, aluminum oxide, lanthanum series oxide(s), zeolite(s) and combinations thereof. The interfacial layer may serve as a catalytically active layer without any further catalytically active material deposited thereon. The interfacial layer may be used in combination with a catalytically active layer. The catalyst may be mixed with the interfacial layer. The interfacial layer may also be formed of two or more compositionally different sublayers. The interfacial layer may have a thickness that is less than one half of the average pore size of the porous support. The interfacial layer thickness may range from about 0.5 to about 100 μm, and in one embodiment from about 1 to about 50 microns. The interfacial layer may be either crystalline or amorphous. The interfacial layer may have a BET surface area of at least about 1 $m^2/g$.

The catalyst may be deposited on the interfacial layer. Alternatively, the catalyst may be simultaneously deposited with the interfacial layer. The catalyst layer may be intimately dispersed on the interfacial layer. That the catalyst layer is "dispersed on" or "deposited on" the interfacial layer includes the conventional understanding that microscopic catalyst particles are dispersed: on the support layer (i.e., interfacial layer) surface, in crevices in the support layer, and in open pores in the support layer.

The catalyst may be in the form of a bed of particulates which may be graded in composition or graded with a thermally conductive inert material. The thermally conductive inert material may be interspersed with the active catalyst. Examples of thermally conductive inert materials that may be used include diamond powder, silicon carbide, aluminum, alumina, copper, graphite, and the like. The catalyst bed fraction may range from about 100% by weight active catalyst to less than about 50% by weight active catalyst. The catalyst bed fraction may range from about 10% to about 90% by weight active catalyst, and in one embodiment from about 25% to about 75% by weight. In an alternate embodiment the thermally conductive inert material may be deployed at the center of the catalyst or within the catalyst particles. The active catalyst may be deposited on the outside, inside or intermittent within a composite structure that includes the thermally conductive inert. The resultant catalyst composite structure may have an effective thermal conductivity when placed in a process microchannel or combustion channel that is at least about 0.3 W/m/K, and in one embodiment at least about 1 W/m/K, and in one embodiment at least about 2 W/m/K.

The catalyst bed may be graded only locally within the process microchannel. For example, a process microchannel may contain a catalyst bed with a first reaction zone and a second reaction zone. The top or bottom (or front or back) of the catalyst bed may be graded in composition whereby a more or less active catalyst is employed in all or part of the first or second reaction zone. The composition that is reduced in one reaction zone may generate less heat per unit volume and thus reduce the hot spot and potential for the production of undesirable by-products, such as methane in a Fischer-Tropsch reaction. The catalyst may be graded with an inert material in the first and/or second reaction zone, in full or in part. The first reaction zone may contain a first composition of catalyst or inert material, while the second reaction zone may contain a second composition of catalyst or inert material.

Different particle sizes may be used in different axial regions of the process microchannels to provide for graded catalyst beds. For example, very small particles may be used in a first reaction zone while larger particles may be used in a second reaction zone. The average particle diameters may be less than half the height or gap of the process microchannels. The very small particles may be less than one-fourth of the process microchannel height or gap. Larger particles may cause lower pressure drops per unit length of the process microchannels and may also reduce the catalyst effectiveness. The effective thermal conductivity of a catalyst bed may be lower for larger size particles. Smaller particles may be used in regions where improved heat transfer is sought throughout the catalyst bed or alternatively larger particles may be used to reduce the local rate of heat generation.

Relatively short contact times, high selectivity to the desired product and relatively low rates of deactivation of the catalyst may be achieved by limiting the diffusion path required for the catalyst. This may be achieved when the catalyst is in the form of a thin layer on an engineered support such as a metallic foam or on the wall of the process microchannel. This may allow for increased space velocities. The thin layer of catalyst may be produced using chemical vapor deposition. This thin layer may have a thickness in the range up to about 1 micron, and in one embodiment in the range from about 0.1 to about 1 micron, and in one embodiment in the range from about 0.1 to about 0.5 micron, and in one embodiment about 0.25 micron. These thin layers may reduce the time the reactants are within the active catalyst structure by reducing the diffusional path. This may decrease the time the reactants spend in the active portion of the catalyst. The result may be increased selectivity to the product and reduced unwanted by-products. An advantage of this mode of catalyst deployment may be that, unlike conventional catalysts in which the active portion of the catalyst may be bound up in an inert low thermal conductivity binder, the active catalyst film may be in intimate contact with either an engineered structure or a wall of the process microchannel. This may leverage high heat transfer rates attainable in the microchannel reactor and allow for close control of temperature. This may result in the ability to operate at increased temperature (faster kinetics) without promoting the formation of undesired by-products, thus producing higher productivity and yield and prolonging catalyst life.

The configuration of the microchannel reactor 110 may be tailored to match the reaction kinetics. Near the entrance or top of a first reaction zone of a process microchannel, the microchannel height or gap may be smaller than in a second reaction zone near the exit or bottom of the process microchannel. Alternatively, the reaction zones may be smaller than half the process microchannel length. For example, a first process microchannel height or gap may be used for the first 25%, 50%, 75%, or 90% of the length of the process microchannel for a first reaction zone, while a larger second height or gap may be used in a second reaction zone downstream from the first reaction zone. This configuration may be suitable for conducting Fischer-Tropsch reactions. Other gradations in the process microchannel height or gap may be used. For example, a first height or gap may be used near the entrance of the microchannel to provide a first reaction zone, a second height or gap downstream from the first reaction zone may be used to provide a second reaction zone, and a third height or gap may be used to provide a third reaction zone near the exit of the microchannel. The first and third heights or gaps may be the same or different. The first and third heights or gaps may be larger or smaller than the second height or gap. The third height or gap may be smaller or larger than the second height or gap. The second height or gap may be larger or smaller than the third height or gap.

The catalyst may be regenerated by flowing a regenerating fluid through the process microchannels combustion channel in contact with the catalyst. The regenerating fluid may comprise hydrogen or a diluted hydrogen stream. The diluent may comprise nitrogen, argon, helium, methane, carbon dioxide, steam, or a mixture of two or more thereof. The temperature of the regenerating fluid may be from about 50 to about 400° C., and in one embodiment about 200 to about 350° C. The pressure within the channels during this regeneration step may range from about 1 to about 40 atmospheres, and in one embodiment about 1 to about 20 atmospheres, and in one embodiment about 1 to about 5 atmospheres. The residence time for the regenerating fluid in the channels may range from about 0.01 to about 1000 seconds, and in one embodiment about 0.1 second to about 100 seconds.

The catalyst may be regenerated by increasing the molar ratio of $H_2$ to CO in the reactant composition to at least about 2.5:1, or at least about 3:1, and flowing the resulting adjusted feed composition through the process microchannels in contact with the catalyst at a temperature in the range from about 150° C. to about 300° C., or in the range from about 180° C. to about 250° C., for a period of time in the range from about 0.1 to about 100 hours, or in one embodiment in the range from about 0.5 to about 20 hours, to provide the regenerated catalyst. The feed composition may be adjusted by interrupting the flow of all feed gases except hydrogen and flowing the hydrogen through the process microchannels in contact with the catalyst. The flow of $H_2$ may be increased to provide for the same contact time used for the reactant composition comprising $H_2$ and CO. The adjusted feed composition may comprise $H_2$ and be characterized by the absence of CO. Once the catalyst is regenerated, the Fischer-Tropsch process may be continued by contacting the regenerated catalyst with the original reactant composition comprising $H_2$ and CO. The catalyst may be regenerated by removing wax and other hydrocarbons from the catalyst (typically by stripping with $H_2$), oxidizing the catalyst with air or other $O_2$ containing gas at an elevated temperature, re-reducing the catalyst, and then activating the catalyst.

EXAMPLE 1

A catalyst precursor is made using the following reagents:

|  | Supplier | Code | Purity |
|---|---|---|---|
| Cobalt nitrate hexahydrate | Sigma-Aldrich | 230375 | 98% |
| Tetraammine platinum hydroxide | Alfa Aesar | 38201-97-7 | 9.3% Pt w/w |
| Silica (SG432) | Grace Davison | (180-300 μm) |  |
| Citric acid monohydrate (CA) | Sigma Aldrich | C1909 | ACS Reagent |
| Perrhenic acid | Sigma Aldrich | 70 wt % solution in water | 99.99% |

Support Preparation 100 g of 16% $TiO_2$-modified silica (expressed as a weight percentage of the catalyst support) is prepared from:

| | |
|---|---|
| Silica (180-300 μm) | 84 g |
| Citric acid monohydrate | 25 g |
| Titanium (IV) bis(ammoniumlactate)dihydroxide solution (TALH) | 118 g (97 mL) |
| Approximate solution volume | 130-135 mL |

The silica bare catalyst support material is dried at 100° C. for 2 hours and allowed to cool to room temperature before impregnation. 25 g citric acid are dissolved in minimum water at 40 to 45° C. and cooled down to less than 30° C. The citric acid solution is then added to 118 g (97 ml) of titanium (IV) bis(ammoniumlactate)dihydroxide solution (TALH) and made up to the required volume of impregnation, which is about 130 to 135 ml, with water. The required amount of silica (84 g, weight determined after drying) is impregnated by spraying with the resulting citric acid-TALH impregnation solution.

Drying is then carried out at 2° C./100° C./5 h (Ramp/Temp/Hold) and calcining is carried out at 2° C./250° C./5 h (Ramp/Temp/Hold). The yield of the modified catalyst support after drying and calcining is about 120 g. The modified catalyst support is dark brown in colour.

Preparation of First Impregnation Solution 25 g of cobalt nitrate hexahydrate (Sigma Aldrich, 98% purity) are dissolved in water and then the solution is heated to 40 to 45° C. until the salt dissolves completely. The minimum required water is used to obtain a clear solution. 0.048 g of perrhenic acid (Sigma Aldrich, 70 wt % solution in water, 99.99% purity) is added to the cobalt nitrate solution and mixed. The resulting solution is cooled to room temperature (less than 30° C.) and made up with water to 19 ml.

Impregnation—1St Step

A first impregnation of the modified catalyst support is carried out by using 19 ml of the cobalt nitrate/perrhenic acid solution to impregnate 20 g of the modified catalyst support. The resulting modified catalyst support is then dried at a temperature that increased at a ramp rate of 2° C./min up to 100° C. The temperature is held at 100° C. for 5 hours. The modified support catalyst is subsequently calcined by increasing the temperature to 200° C. using a ramp rate of 2° C./min and holding the temperature at 200° C. for 3 hours, followed by further increasing the temperature to 250° C. using a ramp rate of 2° C./min and holding the temperature at 250° C. for 1 hour.

Preparation of Impregnation Solution for 2Nd to 4Th Step 12 g of citric acid monohydrate (Sigma Aldrich, ACS Reagent) is dissolved in water. To the clear solution was added 81.4 g of cobalt nitrate hexahydrate (Sigma Aldrich, 98% purity) and then the solution is heated to 40 to 45° C. until the salt dissolves. The minimum required water is used to obtain a clear solution. 0.14 g of perrhenic acid (Sigma Aldrich, 70 wt % solution in water, 99.99% purity) is added to the cobalt nitrate and citric acid solution and mixed. The resulting stock solution is cooled to room temperature (less than 30° C.) and made up with water to 66 to 67 ml.

Impregnation—2Nd to 4Th Steps

A second impregnation step is carried out by using about 22 ml of the stock solution to impregnate the modified catalyst support obtained from the first impregnation step (27.20 g). The modified catalyst support was then dried at a temperature that increases at a ramp rate of 2° C./min up to 100° C. The temperature is held at 100° C. for 5 hours. The modified support catalyst is subsequently calcined by increasing the temperature to 250° C. using a ramp rate of 2° C./min and holding the temperature at 250° C. for 3 hours.

A third impregnation step is carried out by using about 22 ml of the stock solution to impregnate the modified catalyst support obtained from the second impregnation step (34.40 g). The modified catalyst support is then dried at a temperature that increased at a ramp rate of 2° C./min up to 100° C. The temperature is held at 100° C. for 5 hours. The modified support catalyst is subsequently calcined by increasing the temperature to 250° C. using a ramp rate of 2° C./min and holding the temperature at 250° C. for 3 hours.

A fourth impregnation step is carried out by using about 22 ml of the stock solution to impregnate the modified catalyst support obtained from the third impregnation step (41.60 g). The modified catalyst support is then dried at a temperature that increased at a ramp rate of 2° C./min up to 100° C. The temperature is held at 100° C. for 5 hours. The modified support catalyst is subsequently calcined by increasing the temperature to 250° C. using a ramp rate of 2° C./min and holding the temperature at 250° C. for 3 hours.

The four impregnation steps are summarized in Table 1. The total value in Table 1 relates to the total of steps 2 to 4 only.

TABLE 1

| Step | Support wt (g) | $Co(NO_3)_2$ $6H_2O$ (g) (Purity 98%) | $Co(NO_3)_2$ $6H_2O$ (g) | $Co_3O_4$ (g) | Co (g) | Citric acid (g) | Perrhenic acid (g) | % Re (g) | $H_2O$ (ml) | Solution volume (ml) | Mass (g) | % Co |
|---|---|---|---|---|---|---|---|---|---|---|---|---|
| 1 | 20 | 24.49 | 24 | 6.62 | 4.86 | 0.00 | 0.0480 | 0.05 | min. | 19 | 26.6 | 18.2 |
| 2 | 27.2 | 27.14 | 26.6 | 7.33 | 5.38 | 3.84 | 0.0480 | 0.05 | min. | 22 | 34.5 | 29.7 |
| 3 | 34.4 | 27.14 | 26.6 | 7.33 | 5.38 | 3.84 | 0.0480 | 0.05 | min. | 22 | 41.7 | 37.4 |
| 4 | 41.6 | 27.14 | 26.6 | 7.33 | 5.38 | 3.84 | 0.0480 | 0.05 | min. | 22 | 48.9 | 42.9 |
| Total 2-4 |  | 81.43 |  |  |  | 11.52 | 0.14 | 0.20 |  | 66.38 |  |  |

Promoter Addition—5Th Impregnation Step

A promoter addition step is then carried out using 20 g of the catalyst precursor obtained after the four impregnation steps. 0.06 g of tetraammine platinum hydroxide (Alfa Aesar, 9.3% Pt w/w) is added to 9 ml water to make a dilute solution and this solution is used to further impregnate the catalyst precursor. After impregnation, the catalyst is then dried at a temperature that increased at a ramp rate of 2° C./min up to 100° C. The temperature is held at 100° C. for 5 hours. The catalyst is subsequently calcined by increasing the temperature to 250° C. using a ramp rate of 2° C./min and holding the temperature at 250° C. for 3 hours. The resulting catalyst has 0.03% Pt.

EXAMPLE 2

Figure 13:
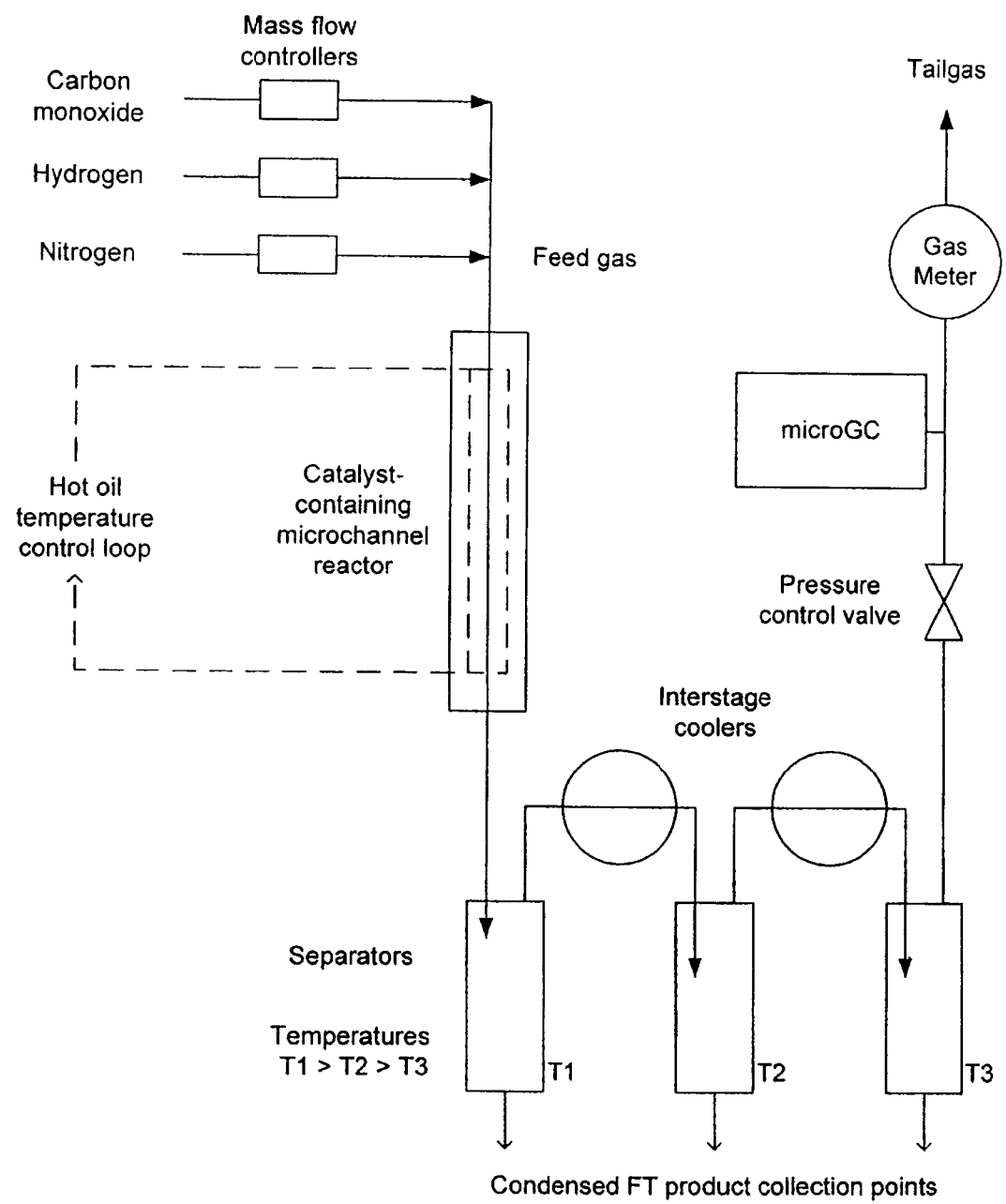
FIG. 13 is a flow sheet illustrating the test procedure used in Example 2.

The catalyst of Example 1 is used in a series of Fischer-Tropsch reactions that are conducted in a microchannel reactor using as the reactant fresh synthesis gas, or a mixture of fresh synthesis gas and tail gas. FIG. 13 is a process flow sheet illustrating the process that is used. The results are indicated in Table 2. The data in Table 2 is generated using a single microchannel reactor. Carbon monoxide (CO), hydrogen ($H_2$), and nitrogen ($N_2$) are delivered separately to the reactor using calibrated mass flow controllers so that the flow of each gas can be changed independently to simulate different process configurations, such as a single reactor stage with a recycle loop. The reaction temperature is controlled with hot oil flowing co-currently in two neighboring microchannels that are not in fluid communication with the reaction chamber. The reaction products and un-reacted gas are separated into condensed and vapor streams in a series of three separators with interstage heat exchangers, and each separator vessel was maintained at a subsequently lower temperature. At the end of the separator train the tailgas (vapor-phase reaction products plus unreacted feed gas) exits the system through a pressure control valve, set to control the pressure at the inlet of the reactor.

Reaction performance is determined by characterizing the outlet stream; the dry tailgas composition was analyzed using an Agilent 3000A micro gas chromatograph and the outlet flow was measured using a gas meter. The outlet flow of any species is calculated by multiplying the mole percent by the total gas flow, standardized to the same reference condition used for the mass flow controller calibration. The performance of the reactor is judged by conversion of CO and selectivity to methane (plus other hydrocarbon species, up to $C_8$). The amount of CO converted is determined by subtracting the outlet CO flow from the calibrated inlet flow. Conversion percent is calculated by dividing the amount of CO converted by the amount of CO delivered to the reactor inlet. The methane ($C_1$) selectivity is calculated by dividing the amount of methane produced by the amount of CO converted.

Abbreviated
CO flow to the reactor: $CO_{in}$
Species mole percent in the tailgas, measured by microGC: [species], e.g. [CO]
Total tailgas outlet flow: $flow_{out}$
$CO_{in}$ is set by calibrated MFC
$CO_{out} = [CO] \times flow_{out}$
CO conversion $= 100\% \times (CO_{in} - CO_{out})/CO_{in}$
C1 selectivity $= 100\% \times flow_{out} \times [C1]/(CO_{in} - CO_{out})$ The condensed FT reaction products are collected from the three separators, weighed to determine production rate, and analyzed separately using an Agilent 7890 gas chromatograph, employing methods derived from ASTM D2887. The GC data is combined proportionally based on the production rate of each phase to generate the full carbon number distribution shown in the associated document.

TABLE 2

| | Long Term Operation Data | | | | | |
|---|---|---|---|---|---|---|
| | Once Through | 1 Stage w/recycle | Once Through | 1 Stage w/recycle | 1 Stage w/recycle | 1 Stage w/recycle |
| TOS Range - Start | 4.2 | 30.0 | 51.0 | 68.4 | 109.9 | 145.1 |
| - End | 20.5 | 46.7 | 60.4 | 107.4 | 142.3 | 182.4 |
| Duration (days) | 16.3 | 16.7 | 9.4 | 39.0 | 32.4 | 37.2 |
| Days Since - Regen | — | — | 11.5 | 58.5 | 93.4 | 133.5 |
| Temperature (C.) | 205.6 | 205.0 | 199.0 | 201.0 | 203.5 | 208.0 |
| Pressure (psig) | 350.0 | 350.0 | 350.0 | 350.0 | 420.0 | 350.0 |
| DP (psid) | 43.6 | 34.0 | 39.2 | 36.7 | 35.1 | 34.1 |
| GHSV | 15652 | 11249 | 13846 | 11612 | 12856 | 11613 |
| CO Prod (v/v/hr) | 3165 | 1949 | 2780 | 1971 | 2239 | 2275 |
| C5+ Prod (g/g/hr) | 1.53 | 0.97 | 1.36 | 0.99 | 1.11 | 1.13 |
| Feed Inerts | 16.50 | 35.00 | 16.50 | 35.00 | 35.00 | 27.00 |
| Feed H2/CO | 2.00 | 1.85 | 2.00 | 1.85 | 1.85 | 1.79 |
| Tail Gas H2/CO | 1.73 | 1.05 | 1.70 | 1.12 | 1.08 | 0.90 |
| Reactor Outlet H2O/H2 | 1.54 | 3.00 | 1.52 | 2.60 | 2.97 | 3.31 |
| Reactor Outlet H2O PP (bar) | 7.49 | 6.04 | 7.56 | 5.82 | 7.33 | 7.31 |
| CO Conv (per pass)* | 72.64% | 75.96% | 72.12% | 74.42% | 76.35% | 74.86% |
| CO2 Select | 0.22% | 0.33% | 0.17% | 0.24% | 0.26% | 0.31% |
| C1 Select | 8.02% | 6.32% | 7.19% | 5.95% | 6.22% | 6.30% |
| C2 Select | 0.67% | 0.55% | 0.61% | 0.49% | 0.53% | 0.61% |
| C3 Select | 1.96% | 1.73% | 2.06% | 1.66% | 1.75% | 1.85% |
| C4 Select | 2.33% | 2.00% | 2.27% | 1.95% | 2.03% | 2.11% |
| C5+ Select (by diff) | 86.81% | 89.07% | 87.70% | 89.71% | 89.21% | 88.83% |
| C5+ Select (by Mat Bal) | | 88.72% | | 89.48% | 89.17% | 88.46% |
| Alpha | | 0.915 | | 0.930 | 0.921 | 0.915 |
| Deactivation Rate (%/day) | | −0.092% | | −0.097% | −0.063% | −0.072% |

TABLE 2-continued

Long Term Operation Data

|  | 1 Stage w/recycle | 1 Stage w/recycle | 1 Stage w/recycle | 1 Stage w/recycle ** | 1 Stage w/recycle ** |
|---|---|---|---|---|---|
| TOS Range - Start | 186.9 | 227.1 | 242.2 | 291.8 | 311.1 |
| - End | 224.6 | 236.4 | 285.3 | 310.6 | 320.2 |
| Duration (days) | 37.6 | 9.3 | 43.0 | 18.8 | 9.1 |
| Days Since - Regen | 175.7 | 187.5 | 236.4 | 261.7 | 271.3 |
| Temperature (C.) | 209.5 | 202.0 | 205.0 | 224.9 | 217.0 |
| Pressure (psig) | 350.0 | 419.4 | 420.0 | 350.0 | 350.0 |
| DP (psid) | 35.2 | 22.6 | 22.8 | 29.4 | 19.9 |
| GHSV | 11612 | 9000 | 9000 | 11612 | 8001 |
| CO Prod (v/v/hr) | 2002 | 1748 | 1730 | 2099 | 1473 |
| C5+ Prod (g/g/hr) | 0.98 | 0.88 | 0.86 | 0.88 | 0.68 |
| Feed Inerts | 35.00 | 28.00 | 28.00 | 28.00 | 28.00 |
| Feed H2/CO | 1.85 | 1.79 | 1.79 | 1.79 | 1.79 |
| Tail Gas H2/CO | 1.02 | 0.88 | 0.74 | 0.72 | 0.64 |
| Reactor Outlet H2O/H2 | 3.02 | 3.43 | 3.97 | 6.15 | 7.80 |
| Reactor Outlet H2O PP (bar) | 5.98 | 9.02 | 9.02 | 6.43 | 6.94 |
| CO Conv (per pass)* | 75.60% | 75.26% | 74.46% | 82.05% | 83.55% |
| CO2 Select | 0.32% | 0.22% | 0.30% | 1.58% | 1.21% |
| C1 Select | 7.28% | 5.24% | 5.81% | 14.43% | 10.04% |
| C2 Select | 0.67% | 0.51% | 0.51% | 0.51% | 0.51% |
| C3 Select | 1.86% | 1.91% | 1.91% | 1.91% | 1.91% |
| C4 Select | 2.30% | 2.11% | 2.11% | 2.11% | 2.11% |
| C5+ Select (by diff) | 87.57% | 90.02% | 89.16% | 75.37% | 82.43% |
| C5+ Select (by Mat Bal) | 87.16% |  |  |  |  |
| Alpha | 0.898 |  |  |  |  |
| Deactivation Rate (%/day) | −0.080% | −0.119% | −0.075% | −0.076% | −0.117% |

*Simulated Single Stage With Recycle Gas Compositions Based on 74% per pass, 91-92% overall (fresh feed) CO conversion
** Last 2 columns Simulated Single Stage With Recycle Gas Compositions Based on 80% per pass, 95% overall (fresh feed) CO conversion While the invention has been explained in relation to various embodiments, it is to be understood that various modifications thereof will become apparent to those skilled in the art upon reading the specification. Therefore, it is to be understood that the invention disclosed herein includes any such modifications that may fall within the scope of the appended claims.

The invention claimed is:

1. A process for conducting a Fischer-Tropsch reaction, comprising:
    flowing a reactant mixture in a microchannel reactor in contact with a catalyst to form a product comprising at least one higher molecular weight hydrocarbon product, the microchannel reactor comprising at least one process microchannel and at least one heat exchange channel in thermal contact with the at least one process microchannel, the catalyst being in the at least one process microchannel, the at least one heat exchange channel having a heat exchange fluid in it for exchanging heat with the at least one process microchannel;
    wherein the product further comprises tail gas, at least part of the tail gas being separated from the higher molecular weight hydrocarbon product and combined with fresh synthesis gas to form the reactant mixture, the volumetric ratio of the fresh synthesis gas to the tail gas in the reactant mixture being in the range from about 1:1 to about 10:1;
    the reactant mixture comprising $H_2$ and CO, the mole ratio of $H_2$ to CO in the reactant mixture based on the concentration of CO in the fresh synthesis gas being in the range from about 1.4:1 to about 2.1:1;
    wherein the conversion of CO from the fresh synthesis gas in the reactant mixture is in the range from about 88% to about 95%, and the deactivation rate of the catalyst is less than about 1.4% per day; and
    the selectivity to methane in the product is in the range from about 0.01 to 10%.

2. The process of claim 1 wherein the catalyst is derived from a catalyst precursor comprising cobalt, a cobalt oxide, or a mixture thereof.

3. The process of claim 2 wherein the catalyst precursor further comprises a support.

4. The process of claim 3 wherein the support comprises a surface modified support wherein the surface modified support comprises a support which is modified by being treated with titania, zirconia, magnesia, chromia, alumina, or a mixture of two or more thereof.

5. The process of claim 3 wherein the support comprises a refractory metal oxide, carbide, carbon, nitride, or a mixture of two or more thereof.

6. The process of claim 3 wherein the support comprises alumina, zirconia, silica, titania, or a mixture of two or more thereof.

7. The process of claim 3 wherein the support comprises silica and its surface is modified by being treated with titania.

8. The process of claim 3 wherein the surface of the support is amorphous.

9. The process of claim 2 wherein the cobalt oxide comprises $Co_3O_4$ and/or CoO.

10. The process of claim 4 wherein the surface of the surface modified support is such that neutralization requires at least about 0.2 μmol $NH_3$ per square meter.

11. The process of claim 3 wherein the support for the catalyst precursor has a FT-IR band intensity at about 950:980 $cm^{-1}$ of at least about 1.2.

12. The process of claim 9 wherein the $Co_3O_4$ is in the form of particulates, the numerical average particle diameter of the $Co_3O_4$ being less than about 12 nanometers as determined by XRD.

13. The process of claim 2 wherein the catalyst precursor further comprises a noble metal.

14. The process of claim 1 wherein the microchannel reactor comprises a plurality of the process microchannels and a plurality of the heat exchange channels.

15. The process of claim 1 wherein the microchannel reactor comprises a plurality of the process microchannels and a plurality of the heat exchange channels, each heat exchange channel being in thermal contact with at least one process microchannel, at least one manifold for flowing the reactant mixture into the process microchannels, at least one manifold for flowing product out of the process microchannels, at least one manifold for flowing a heat exchange fluid into the heat exchange channels, and at least one manifold for flowing the heat exchange fluid out of the heat exchange channels.

16. The process of claim 1 wherein a plurality of the microchannel reactors are positioned in a vessel, each microchannel reactor comprising a plurality of the process microchannels and a plurality of the heat exchange channels, each heat exchange channel being in thermal contact with at least one process microchannel, the vessel being equipped with a manifold for flowing the reactant mixture to the process microchannels, a manifold for flowing the product from the process microchannels, a manifold for flowing a heat exchange fluid to the heat exchange channels, and a manifold for flowing the heat exchange fluid from the heat exchange channels.

17. The process of claim 16 wherein the vessel contains from 1 to about 1000 microchannel reactors.

18. The process of claim 1 wherein the at least one process microchannel has an internal dimension of width or height of up to about 10 mm.

19. The process of claim 1 wherein the at least one process microchannel has a length of up to about 10 meters.

20. The process of claim 1 wherein the at least one process microchannel and the at least one heat exchange channel are made of a material comprising: aluminum; titanium; nickel; copper; an alloy of any of the foregoing metals; steel; monel; inconel; brass; quartz; silicon; or a combination of two or more thereof.

21. The process of claim 1 wherein the reactant mixture flows in the at least one process microchannel and contacts surface features in the process microchannel, the contacting of the surface features imparting a disruptive flow to the reactant mixture.

22. The process of claim 1 wherein the at least one heat exchange channel comprises a microchannel.

23. The process of claim 1 wherein the catalyst is in the form of particulate solids.

24. The process of claim 1 wherein the catalyst is coated on interior walls of the at least one process microchannels or grown on interior walls of the at least one process microchannels.

25. The process of claim 1 wherein the catalyst is supported on a support having a flow-by configuration, a flow-through configuration, or a serpentine configuration.

26. The process of claim 1 wherein the catalyst is supported on a support having the configuration of a foam, felt, wad, fin, or a combination of two or more thereof.

27. The process of claim 1 wherein the catalyst is supported on a support in the form of a fin assembly comprising a plurality of fins.

28. The process of claim 1 wherein the catalyst is supported on corrugated inserts, the corrugated inserts being positioned in slots within the microchannel reactor.

29. The process of claim 1 wherein the at least one process microchannel has at least one heat transfer wall and the heat flux for heat exchange within the microchannel reactor is in the range from about 0.01 to about 500 watts per square centimeter of surface area of the at least one heat transfer wall.

30. The process of claim 1 wherein the pressure within the at least one process microchannel is in the range up to about 50 atmospheres.

31. The process of claim 1 wherein the temperature in the at least one process microchannel is in the range from about 150 to about 300° C.

32. The process of claim 1 wherein the contact time of the reactant mixture with the catalyst within the at least one process microchannel is up to about 2000 milliseconds.

33. The process of claim 1 wherein the at least one higher molecular weight hydrocarbon product comprises one or more hydrocarbons boiling at a temperature of at least about 30° C. at atmospheric pressure.

34. The process of claim 1 wherein the at least one higher molecular weight hydrocarbon product comprises one or more hydrocarbons boiling above a temperature of about 175° C. at atmospheric pressure.

35. The process of claim 1 wherein the at least one higher molecular weight hydrocarbon product comprises one or more paraffins and/or one or more olefins of 2 to about 200 carbon atoms.

36. The process of claim 1 wherein the at least one higher molecular weight hydrocarbon product comprises one or more olefins, one or more normal paraffins, one or more isoparaffins, or a mixture of two or more thereof.

37. The process of claim 1 wherein the at least one higher molecular weight hydrocarbon product is further processed using separation, fractionation, hydrocracking, hydroisomerizing, dewaxing, or a combination of two or more thereof.

38. The process of claim 1 wherein the at least one higher molecular weight hydrocarbon product is further processed to form an oil of lubricating viscosity or a middle distillate fuel.

39. The process of claim 1 wherein the at least one higher molecular weight hydrocarbon product is further processed to form a fuel.

40. The process of claim 1 wherein the process microchannel has fluid flowing in it in one direction, the at least one heat exchange channel has fluid flow in a direction that is co-current or counter-current to the flow of fluid in the at least one process microchannel.

41. The process of claim 1 wherein the at least one process microchannel has fluid flowing in it in one direction, the at least one heat exchange channel has fluid flowing in it in a direction that is cross-current to the flow of fluid in the at least one process microchannel.

42. The process of claim 1 wherein a tailored heat exchange profile is provided along the length of the at least one process microchannel, the local release of heat given off by the reaction conducted in the at least one process microchannel being matched with cooling provided by the at least one heat exchange channel.

43. The process of claim 1 wherein the catalyst comprises a graded catalyst.

44. The process of claim 1 wherein the Quality Index Factor for the microchannel reactor is less than about 50%.

45. The process of claim 1 wherein the superficial velocity for fluid flowing in the at least one process microchannel is at least about 0.01 m/s.

46. The process of claim 1 wherein the space velocity for fluid flowing in the at least one process microchannel is at least about 1000 $hr^{-1}$.

47. The process of claim 1 wherein the pressure drop for fluid flowing in the at least one process microchannel is up to about 10 atmospheres per meter.

48. The process of claim 1 wherein the Reynolds number for the flow of fluid in the at least one process microchannel is in the range from about 10 to about 4000.

49. The process of claim 1 wherein the microchannel reactor comprises a plurality of the process microchannels, the process microchannels being formed by positioning a waveform between planar sheets.

50. The process of claim 49 wherein the microchannel reactor further comprises a plurality of the heat exchange channels in thermal contact with the process microchannels, the heat exchange channels being formed by positioning a waveform between planar sheets.

51. The process of claim 1 wherein the microchannel reactor comprises a plurality of plates in a stack defining a plurality of Fischer-Tropsch process layers and a plurality of heat exchange layers, each plate having a peripheral edge, the peripheral edge of each plate being welded to the peripheral edge of the next adjacent plate to provide a perimeter seal for the stack.

52. The process of claim 1 wherein the deactivation rate of the catalyst is less than a loss of about 0.2% CO conversion per day.

53. The process of claim 1 wherein the product further comprises $H_2O$ and $H_2$, the $H_2O$ partial pressure for the product being in the range from about 3 to about 10 bar, the $H_2O/H_2$ molar ratio for the product being in the range from about 1:1 to about 5:1.

54. The process of claim 2 wherein the catalyst precursor comprises from about 10% to about 60% by weight cobalt based on the weight of the metal as a percentage of the total weight of the catalyst precursor.

55. The process of claim 2 wherein the catalyst precursor comprises from about 35% to about 60% by weight cobalt based on the weight of the metal as a percentage of the total weight of the catalyst precursor.

56. A process for conducting a Fischer-Tropsch reaction, comprising:
   flowing a reactant mixture in a microchannel reactor in contact with a catalyst to form a product comprising at least one higher molecular weight hydrocarbon product, the microchannel reactor comprising at least one process microchannel and at least one heat exchange channel in thermal contact with the at least one process microchannel, the catalyst being in the at least one process microchannel, the at least one heat exchange channel having a heat exchange fluid in it for exchanging heat with the at least one process microchannel, the temperature in the at least one process microchannel being in the range from about 175° C. to about 225° C.;
   wherein the product further comprises tail gas, at least part of the tail gas being separated from the higher molecular weight hydrocarbon product and combined with fresh synthesis gas to form the reactant mixture, the volumetric ratio of the fresh synthesis gas to the tail gas in the reactant mixture being in the range from about 1:1 to about 10:1;
   the reactant mixture comprising $H_2$ and CO, the mole ratio of $H_2$ to CO in the reactant mixture based on the concentration of CO in the fresh synthesis gas being in the range from about 1.4:1 to about 2.1:1;
   wherein the conversion of CO from the fresh synthesis gas in the reactant mixture is in the range from about 88% to about 95%, and the deactivation rate of the catalyst is less than about 1.4% per day; and
   the selectivity to methane in the product is in the range from about 0.01 to 10%.

57. A process for conducting a Fischer-Tropsch reaction, comprising:
   flowing a reactant mixture in a microchannel reactor in contact with a catalyst to form a product comprising at least one higher molecular weight hydrocarbon product, the microchannel reactor comprising at least one process microchannel and at least one heat exchange channel in thermal contact with the at least one process microchannel, the catalyst being in the at least one process microchannel, the at least one heat exchange channel having a heat exchange fluid in it for exchanging heat with the at least one process microchannel, the heat flux for heat exchange in the microchannel reactor being in the range from about 0.2 to about 5 $W/cm^2$;
   wherein the product further comprises tail gas, at least part of the tail gas being separated from the higher molecular weight hydrocarbon product and combined with fresh synthesis gas to form the reactant mixture, the volumetric ratio of the fresh synthesis gas to the tail gas in the reactant mixture being in the range from about 1:1 to about 10:1;
   the reactant mixture comprising $H_2$ and CO, the mole ratio of $H_2$ to CO in the reactant mixture based on the concentration of CO in the fresh synthesis gas being in the range from about 1.4:1 to about 2.1:1;
   wherein the conversion of CO from the fresh synthesis gas in the reactant mixture is in the range from about 88% to about 95%, and the deactivation rate of the catalyst is less than about 1.4% per day; and
   the selectivity to methane in the product is in the range from about 0.01 to 10%.

58. A process for conducting a Fischer-Tropsch reaction, comprising:
   flowing a reactant mixture in a microchannel reactor in contact with a catalyst to form a product comprising at least one higher molecular weight hydrocarbon product, the microchannel reactor comprising at least one process microchannel and at least one heat exchange channel in thermal contact with the at least one process microchannel, the catalyst being in the at least one process microchannel, the length of the at least one process microchannel being in the range from about 0.2 to about 3 meters, the at least one heat exchange channel having a heat exchange fluid in it for exchanging heat with the at least one process microchannel;
   wherein the product further comprises tail gas, at least part of the tail gas being separated from the higher molecular weight hydrocarbon product and combined with fresh synthesis gas to form the reactant mixture, the volumetric ratio of the fresh synthesis gas to the tail gas in the reactant mixture being in the range from about 1:1 to about 10:1;
   the reactant mixture comprising $H_2$ and CO, the mole ratio of $H_2$ to CO in the reactant mixture based on the concentration of CO in the fresh synthesis gas being in the range from about 1.4:1 to about 2.1:1;
   wherein the conversion of CO from the fresh synthesis gas in the reactant mixture is in the range from about 88% to about 95%, and the deactivation rate of the catalyst is less than about 1.4% per day; and
   the selectivity to methane in the product is in the range from about 0.01 to 10%.

59. A process for conducting a Fischer-Tropsch reaction, comprising:
   flowing a reactant mixture in a microchannel reactor in contact with a catalyst to form a product comprising at least one higher molecular weight hydrocarbon product, the microchannel reactor comprising at least one process microchannel and at least one heat exchange channel in thermal contact with the at least one process microchannel, the catalyst being in the at least one process microchannel, the at least one heat exchange channel having a heat exchange fluid in it exchanging heat with the at least one process microchannel;

wherein the product further comprises tail gas, at least part of the tail gas being separated from the higher molecular weight hydrocarbon product and combined with fresh synthesis gas to form the reactant mixture, the volumetric ratio of the fresh synthesis gas to the tail gas in the reactant mixture being in the range from about 1:1 to about 10:1;

the reactant mixture comprising $H_2$ and CO, the mole ratio of $H_2$ to CO in the reactant mixture based on the concentration of CO in the fresh synthesis gas being in the range from about 1.4:1 to about 2.1:1, the contact time of the reactant mixture with the catalyst being in the range from 20 to about 500 milliseconds;

wherein the conversion of CO from the fresh synthesis gas in the reactant mixture is in the range from about 88% to about 95%, and the deactivation rate of the catalyst is less than about 1.4% per day; and the selectivity to methane in the product is in the range from about 0.01 to 10%.

60. A process for conducting a Fischer-Tropsch reaction, comprising:

flowing a reactant mixture in a microchannel reactor in contact with a catalyst to form a product comprising at least one higher molecular weight hydrocarbon product, the microchannel reactor comprising at least one process microchannel and at least one heat exchange channel in thermal contact with the at least one process microchannel, the catalyst being in the at least one process microchannel, the length of the at least one process microchannel being in the range from about 0.2 to about 3 meters, the at least one heat exchange channel having a heat exchange fluid in it for exchanging heat with the at least one process microchannel;

wherein the product further comprises tail gas, at least part of the tail gas being separated from the higher molecular weight hydrocarbon product and combined with fresh synthesis gas to form the reactant mixture, the volumetric ratio of the fresh synthesis gas to the tail gas in the reactant mixture being in the range from about 1:1 to about 10:1;

the reactant mixture comprising $H_2$ and CO, the mole ratio of $H_2$ to CO in the reactant mixture based on the concentration of CO in the fresh synthesis gas being in the range from about 1.4:1 to about 2.1:1, the contact time of the reactant mixture with the catalyst being in the range from about 20 to about 500 milliseconds;

wherein the conversion of CO from the fresh synthesis gas in the reactant mixture is in the range from about 88% to about 95%, and the deactivation rate of the catalyst is less than about 1.4% per day; and the selectivity to methane in the product is in the range from about 0.01 to 10%.

61. A process for conducting a Fischer-Tropsch reaction, comprising:

flowing a reactant mixture in a microchannel reactor in contact with a catalyst to form a product comprising at least one higher molecular weight hydrocarbon product, the microchannel reactor comprising at least one process microchannel and at least one heat exchange channel in thermal contact with the at least one process microchannel, the catalyst being in the at least one process microchannel, the length of the at least one process microchannel being in the range from about 0.2 to about 3 meters, the at least one heat exchange channel having a heat exchange fluid in it for exchanging heat with the at least one process microchannel, the heat flux for heat exchange in the microchannel reactor being in the range from about 0.2 to about 5 $W/cm^2$;

wherein the product further comprises tail gas, at least part of the tail gas being separated from the higher molecular weight hydrocarbon product and combined with fresh synthesis gas to form the reactant mixture, the volumetric ratio of the fresh synthesis gas to the tail gas in the reactant mixture being in the range from about 1:1 to about 10:1;

the reactant mixture comprising $H_2$ and CO, the mole ratio of $H_2$ to CO in the reactant mixture based on the concentration of CO in the fresh synthesis gas being in the range from about 1.4:1 to about 2.1:1, the contact time of the reactant mixture with the catalyst being in the range from about 20 to about 500 milliseconds;

wherein the conversion of CO from the fresh synthesis gas in the reactant mixture is in the range from about 88% to about 95%, and the deactivation rate of the catalyst is less than about 1.4% per day; and the selectivity to methane in the product is in the range from about 0.01 to 10%.

62. A process for conducting a Fischer-Tropsch reaction, comprising:

flowing a reactant mixture in a microchannel reactor in contact with a catalyst to form a product comprising at least one higher molecular weight hydrocarbon product, the microchannel reactor comprising at least one process microchannel and at least one heat exchange channel in thermal contact with the at least one process microchannel, the catalyst being in the at least one process microchannel, the at least one heat exchange channel having a heat exchange fluid in it for exchanging heat with the at least one process microchannel;

wherein the product further comprises tail gas, at least part of the tail gas being separated from the higher molecular weight hydrocarbon product and combined with fresh synthesis gas to form the reactant mixture, the volumetric ratio of the fresh synthesis gas to the tail gas in the reactant mixture being in the range from about 1:1 to about 10:1;

the reactant mixture comprising $H_2$ and CO, the mole ratio of $H_2$ to CO in the reactant mixture based on the concentration of CO in the fresh synthesis gas being in the range from about 1.4:1 to about 2.1:1;

wherein the conversion of CO from the fresh synthesis gas in the reactant mixture is in the range from about 88% to about 95%, and the gas hourly space velocity for the flow of fluid in the at least one process microchannel being in the range from about 1000 to about 20,000 $hr^{-1}$; and the selectivity to methane in the product is in the range from about 0.01 to 10%.

* * * * *